United States Patent
Sakurai et al.

(10) Patent No.: US 10,322,860 B2
(45) Date of Patent: Jun. 18, 2019

(54) OUTER BAG FOR DISPOSABLE BODY WARMER PACKAGING AND DISPOSABLE BODY WARMER

(71) Applicant: KOBAYASHI PHARMACEUTICAL CO., LTD., Osaka-shi, Osaka (JP)

(72) Inventors: Yuki Sakurai, Osaka (JP); Tsuyoshi Igaue, Osaka (JP)

(73) Assignee: KOBAYASHI PHARMACEUTICAL CO., LTD., Osaka-shi (JP)

(*) Notice: Subject to any disclaimer, the term of this patent is extended or adjusted under 35 U.S.C. 154(b) by 0 days.

(21) Appl. No.: 16/064,988

(22) PCT Filed: Dec. 25, 2015

(86) PCT No.: PCT/JP2015/086264
§ 371 (c)(1),
(2) Date: Jun. 21, 2018

(87) PCT Pub. No.: WO2017/109944
PCT Pub. Date: Jun. 29, 2017

(65) Prior Publication Data
US 2019/0009960 A1    Jan. 10, 2019

(51) Int. Cl.
*B65D 65/40* (2006.01)
*A61F 7/03* (2006.01)
(Continued)

(52) U.S. Cl.
CPC ............. *B65D 65/40* (2013.01); *A61F 7/03* (2013.01); *A61F 7/034* (2013.01); *B32B 27/30* (2013.01);
(Continued)

(58) Field of Classification Search
CPC ........ B65D 65/40; B65D 65/22; B65D 81/24; A61F 7/03; A61F 7/034; A61F 2007/038; B32B 27/30
See application file for complete search history.

(56) References Cited

FOREIGN PATENT DOCUMENTS

| JP | 01-117320 U | 8/1989 |
|---|---|---|
| JP | 04-048182 U | 4/1992 |

(Continued)

OTHER PUBLICATIONS

International Search Report for PCT/JP2015/086264 (PCT/ISA/210) dated Feb. 23, 2016.
(Continued)

*Primary Examiner* — Michael C Miggins
(74) *Attorney, Agent, or Firm* — Birch, Stewart, Kolasch & Birch, LLP

(57) ABSTRACT

An outer bag for disposable body warmer packaging and a disposable body warmer are provided that are excellent in a gas barrier property that inhibits permeation of oxygen gas, water vapor, and the like, which can allow swelling due to hydrogen gas generated during a storage period to be prevented.

Provided is an outer bag for disposable body warmer packaging having an accommodating portion accommodating a disposable body warmer accommodated in an air-permeable inner bag and generating heat through contact with air, the outer bag comprising a low air-permeability portion having an oxygen permeability of 1.5 to 20 cc/m²·day·atm measured at 20° C. and 90% RH and having a water vapor permeability of 0.05 to 10 g/m²·day measured at 40° C. and 90% RH; and an air-impermeable portion having an oxygen permeability of 1.3 cc/m²·day·atm or lower measured at 20° C. and 90% RH and a water vapor permeability of 2.0 g/m²·day or lower measured at 40° C. and 90% RH, wherein (Continued)

a ratio of an area of the low air-permeability portion to a total internal area of the accommodating portion is 15 to 75%.

10 Claims, 15 Drawing Sheets

(51) Int. Cl.
*B32B 27/30* (2006.01)
*B65D 81/24* (2006.01)
*B65D 65/22* (2006.01)

(52) U.S. Cl.
CPC ........ *B65D 81/24* (2013.01); *A61F 2007/038* (2013.01); *B65D 65/22* (2013.01)

(56) References Cited

FOREIGN PATENT DOCUMENTS

| | | |
|---|---|---|
| JP | 11-239584 A | 9/1999 |
| JP | 2003-231221 A | 8/2003 |
| JP | 3107759 U | 2/2005 |
| JP | 2006-347582 A | 12/2006 |

OTHER PUBLICATIONS

International Search Report for PCT/JP2015/086269 (PCT/ISA/210) dated Feb. 23, 2016.
Written Opinion of the International Searching Authority for PCT/JP2015/086264 (PCT/ISA/237) dated Feb. 23, 2016.

(a)

(b)

(a)   (b)

(a)

(b)

(a)

(b)

(a)

(b)

(a)

(b)

(a)        (b)

OUTER BAG FOR DISPOSABLE BODY WARMER PACKAGING AND DISPOSABLE BODY WARMER

TECHNICAL FIELD

The present invention relates to an outer bag for disposable body warmer packaging, and a disposable body warmer.

BACKGROUND ART

A disposable body warmer is a body warmer that utilizes heat generation caused by the oxidation action of iron powders. In the disposable body warmer, usually, an inner bag including an air-permeable bag of a non-woven fabric, paper, or the like which accommodates an exothermic composition containing iron powders as an exothermic element, a salt as an oxidation catalyst, activated carbon for intake of oxygen, water for oxidizing iron, a water-retaining agent for retaining the water, and the like, is accommodated and airtightly packaged in an outer bag made of an air-impermeable film cutting off contact with air in an unused state.

An outer bag for disposable body warmer packaging is required to be excellent in gas barrier property for inhibiting permeation of air, in particular, oxygen gas, water vapor, and the like. If the outer bag for disposable body warmer packaging is poor in its gas barrier property against oxygen gas and water vapor, any gas and water vapor in the outer bag for disposable body warmer packaging will escape outside during storage for a long period, producing a depressurized (vacuum) state and consequently causing the outer bag to be depressed, which is not preferable in terms of appearance. In addition, when such an outer bag in a depressurized (vacuum) state is stored for a long period and thereafter used as a disposable body warmer, the duration of heat generation thereof is often short. As an air-impermeable film forming the outer bag for disposable body warmer packaging, a multilayer film is generally used in which a gas barrier layer is provided on a sealant layer and a heat-resistant resin layer is provided as an outermost layer. Two of such air-impermeable multilayer films are stacked each other and the peripheries of the sealant layers located inward are heat-sealed to each other into the form of a bag. The outer bag for disposable body warmer packaging is thus manufactured.

Meanwhile, it is known that a trace amount of hydrogen gas is generated when a disposable body warmer is stored in an unused state for a long period. The outer bag for disposable body warmer packaging becomes swollen due to the hydrogen gas, and this is not preferable in terms of appearance. In addition, the outer bag is broken when the swelling reaches its limit, and an exothermic composition accommodated in an inner bag is oxidized to generate heat, thereby causing the function as a disposable body warmer to be impaired. For this reason, hydrogen gas permeability is required to such an extent that the outer bag for disposable body warmer packaging is not swollen during the long storage period. However, as described above, it is also required that the outer bag for disposable body warmer packaging excel in the gas barrier property for inhibiting permeation of oxygen gas, water vapor, and the like. As a result, when the bas barrier property of the air-impermeable film forming the outer bag for disposable body warmer packaging is made higher, the hydrogen gas permeability is decreased, causing swelling during the long storage period.

As an outer bag for disposable body warmer packaging that takes the hydrogen gas permeability into consideration, an outer bag for disposable body warmer packaging has been proposed which includes a plastic film and a vapor-deposited layer obtained by vapor deposition of metal such as aluminum on the plastic film, where film exposure portions without any vapor-deposited layer are scattered provided on the surface of the plastic film, the total area of the exposure portions falls within the range of $1/1000$ to $1/10$ to the surface area of the outer bag (PTL 1). In PTL 1, storage experimentation where three-month storage at a temperature of 40° C. is performed is specifically illustrated. Although this condition indicates that the experimentation illustrated therein is equivalent to 1.5-year storage experimentation at room temperature, it cannot be said to be sufficient in terms of temperature or time. Thus, an actual outer bag for disposable body warmer packaging which can withstand severer storage conditions may be required.

As described above, although various outer bags for disposable body warmer packaging have been proposed, they still leave room for improvement and an outer bag for disposable body warmer packaging and disposable body warmer are required which can ensure an optimum gas permeation property and gas barrier property as a product over a long period.

CITATION LIST

Patent Literature

PTL 1: Japanese Utility Model Laid-Open No. H04-048182

SUMMARY OF INVENTION

Technical Problem

In view of the above, an object of the present invention is to provide an outer bag for disposable body warmer packaging and disposable body warmer that are excellent in a gas barrier property that selectively inhibits permeation of oxygen gas, water vapor and the like, which can allow swelling due to hydrogen gas generated during a storage period to be prevented.

Solution to Problem

The present inventors have made intensive studies in order to solve the above problem and, as a result, have found that an outer bag for disposable body warmer packaging having an accommodating portion accommodating a disposable body warmer accommodated in an air-permeable inner bag and generating heat through contact with air, the outer bag including a low air-permeability portion having an oxygen permeability of 1.5 to 20 cc/m$^2$·day·atm measured at 20° C. and 90% RH and a water vapor permeability of 0.05 to 10 g/m$^2$·day measured at 40° C. and 90% RH; and an air-impermeable portion having an oxygen permeability of 1.3 cc/m$^2$·day·atm or lower measured at 20° C. and 90% RH and a water vapor permeability of 2.0 g/m$^2$·day or lower measured at 40° C. and 90% RH, a ratio of an area of the low air-permeability portion to a total internal area of the accommodating portion being 15 to 75%, can achieve optimum oxygen gas permeability, water vapor permeation property, and hydrogen gas permeability without impairing the seal strength, impact resistance, and weatherability, and this knowledge has led to completion of the present invention.

The specific implementations of the disposable body warmer of the present invention are as follows:

[1] An outer bag for disposable body warmer packaging having an accommodating portion accommodating a disposable body warmer accommodated in an air-permeable inner bag, the outer bag comprising a low air-permeability portion having an oxygen permeability of 1.5 to 20 cc/m²·day·atm measured at 20° C. and 90% RH and having a water vapor permeability of 0.05 to 10 g/m²·day measured at 40° C. and 90% RH, and an air-impermeable portion having an oxygen permeability of 1.3 cc/m²·day·atm or lower measured at 20° C. and 90% RH and a water vapor permeability of 2.0 g/m²·day or lower measured at 40° C. and 90% RH, and wherein a ratio of an area of the low air-permeability portion to a total internal area of the accommodating portion is 15 to 75%.

[2] The outer bag for disposable body warmer packaging according to [1], wherein a ratio of area of the low air-permeability portion to a total internal area of the accommodating portion is 50%.

[3] The outer bag for disposable body warmer packaging according to [1] or [2], wherein the low air-permeability portion has a first substrate and a low air-permeability layer laminated on the first substrate, and the air-impermeable portion has a second substrate and an air-impermeable layer laminated on the second substrate, and the first substrate and the second substrate are heat-sealed.

[4] The outer bag for disposable body warmer packaging according to [1] or [2], wherein a low air-permeability layer and an air-impermeable layer are provided on one sealant layer, and the low air-permeability portion has the low air-permeability layer, and the air-impermeable portion has the air-impermeable layer.

[5] The outer bag for disposable body warmer packaging according to [1] or [2], wherein a low air-permeability layer and an air-impermeable layer are provided on one sealant layer, and the low air-permeability portion has the low air-permeability layer, and the air-impermeable portion has the low air-permeability layer and the air-impermeable layer.

[6] The outer bag for disposable body warmer packaging according to any one of [1] to [5], wherein the outer bag for disposable body warmer packaging has at least one heat-sealed portion formed by heat-sealing one or more laminated sheets, and the low air-permeability portion is provided in at least a part of a region adjacent to the heat-sealed portion.

[7] The outer bag for disposable body warmer packaging according to any one of [3] to [5], wherein the low air-permeability layer comprises a homopolymer or copolymer of vinylidene chloride, and the air-impermeable layer contains a metal or metal oxide.

[8] A disposable body warmer packaged by the outer bag according to any one of [1] to [7].

Advantageous Effects of Invention

The outer bag for disposable body warmer packaging of the present invention has an optimum gas barrier property without impairing seal strength, impact resistance, and weatherability as an outer bag for disposable body warmer packaging that blocks permeation of oxygen gas and water vapors and allows permeation of hydrogen gas.

The disposable body warmer of the present invention is capable of preventing swelling caused by hydrogen gas generated while it is stored and degradation of the exothermic composition due to permeation of oxygen gas and water vapors, so that the body warmer can be stored for a long period without impairing the functionality as a disposable body warmer.

DESCRIPTION OF EMBODIMENTS

Figure 1A:
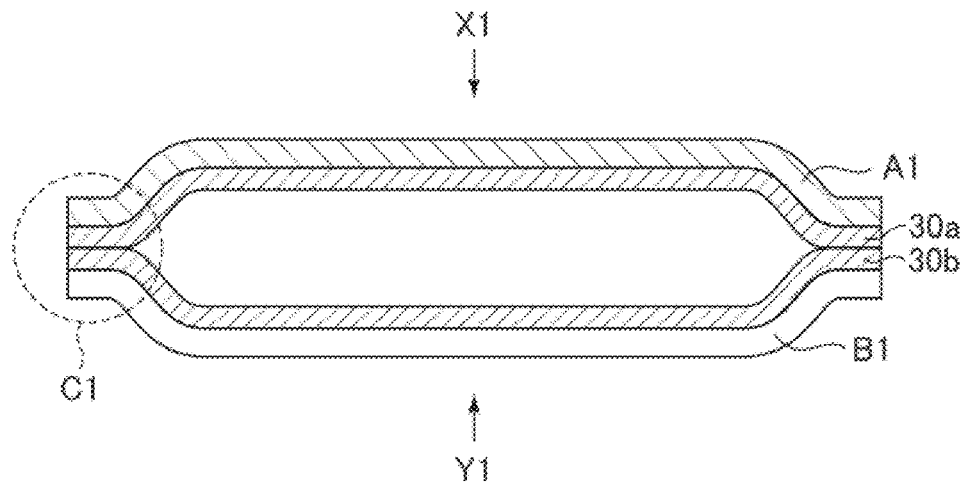
FIG. 1A is a cross-sectional view of an outer bag for disposable body warmer packaging in Embodiment 1 of the present invention.

The outer bag for disposable body warmer packaging and the disposable body warmer of the present invention will be described below with reference to the drawings.

The present invention provides an outer bag for disposable body warmer packaging having an accommodating portion accommodating a disposable body warmer accommodated in an air-permeable inner bag, the outer bag comprising a low air-permeability portion having an oxygen permeability of 1.5 to 20 cc/m²·day·atm measured at 20° C. and 90% RH and a water vapor permeability of 0.05 to 10 g/m²·day measured at 40° C. and 90% RH, and an air-impermeable portion having an oxygen permeability of 1.3 cc/m²·day·atm or lower measured at 20° C. and 90% RH and a water vapor permeability of 2.0 g/m²·day or lower measured at 40° C. and 90% RH, wherein a ratio of an area of the low air-permeability portion to a total internal area of the accommodating portion is 15 to 75%.

The oxygen permeability of the low air-permeability portion (at 20° C. and 90% RH) is 1.5 to 20 cc/(m²·day·atm), preferably 2.0 to 15 cc/(m²·day·atm), and more preferably 2.0 to 10 cc/(m²·day·atm). Also, the water vapor permeability in the low air-permeability portion (at 40° C. and 90% RH) is 0.05 to 10 g/(m²·day), and preferably 1.0 to 5.0 g/(m²·day).

The oxygen permeability of the air-impermeable portion (at 20° C. and 90% RH) is 1.3 cc/(m²·day·atm) or lower, preferably 0.01 to 1.3 cc/(m²·day·atm), more preferably 0.01 to 1.15 cc/(m²·day·atm), and most preferably 0.01 to 1.0 cc/(m²·day·atm). Also, the water vapor permeability in the air-impermeable portion (at 40° C. and 90% RH) is 2.0 g/(m²·day) or lower, preferably 0.01 to 2.0 g/(m²·day), and more preferably 0.01 to 1.5 g/(m²·day).

The outer bag for disposable body warmer packaging of the present invention can satisfy the conflicting requirements of allowing hydrogen gas generated inside of the bag to escape to an outside of the bag and preventing intrusion of oxygen gas and water vapor from the outside into the inside of the bag by virtue of controlling the ratios of the low air-permeability portion and the air-impermeable portion to the internal area of the accommodating portion. The ratio of the area of the low air-permeability portion to the internal area of the accommodating portion is 15 to 75%, preferably 45 to 55%, and 50% will be preferable as a ratio of area that allows for production by a simplified scheme. The ratio of the area of the air-impermeable portion to the internal area of the accommodating portion is 25 to 85%, preferably 45 to 55%, and 50% will be preferable as a ratio of area that allows for production by a simplified scheme. The sum of the low air-permeability portion and the air-impermeable portion is 100%.

In the outer bag for disposable body warmer packaging of the present invention, the oxygen permeability and the water vapor permeability of the low air-permeability portion and the air-impermeable portion are defined within the above-identified numerical ranges, and the ratio of area of the low air-permeability portion or the ratio of the area of the air-impermeable portion to the total internal area of the accommodating portion of the outer bag for disposable body warmer packaging is defined within the above-identified numerical range. Thereby, it is made possible to achieve the effects that it is excellent in its gas barrier property that inhibits permeation of oxygen gas, water vapor, and the like, which can allow swelling due to hydrogen gas generated during a storage period to be prevented. For stable and long-term storage of the disposable body warmer, it is required that the oxygen permeability and the water vapor permeability of the low air-permeability portion and the air-impermeable portion, and the ratio of the area of the low air-permeability portion or the ratio of the area of the air-impermeable portion to the total internal area of the accommodating portion of the outer bag for disposable body warmer packaging both fall within the above-identified ranges. If either of them fails to fall within the corresponding range, the desired effects will not be obtained.

In general, an outer bag for disposable body warmer packaging is formed in the form of a bag through publicly known heat-sealing of various types such as stacking a plurality of laminated sheets each made of multiple layers including a sealant layer and subjecting them to four-side sealing; winding a laminated sheet and subjecting it to three-side sealing or three-side pillow, and the like. The present invention is an outer bag for disposable body warmer packaging which includes a low air-permeability layer and an air-impermeable layer as the layers to be laminated on a sealant layer, and is formed such that the low air-permeability portion and the air-impermeable portion will have predetermined ratios through controlling the modes of lamination of the low air-permeability layer and the air-impermeable layer.

In the outer bag for disposable body warmer packaging of the present invention, the low air-permeability portion has the first substrate and the low air-permeability portion laminated on the first substrate. The air-impermeable portion has the second substrate and the air-impermeable portion laminated on the second substrate. The first substrate and the second substrate are heat-sealed.

Also, in the outer bag for disposable body warmer packaging of the present invention, the low air-permeability layer and the air-impermeable layer are provided on one sealant layer, and the low air-permeability portion has the low air-permeability layer, and the air-impermeable portion has the air-impermeable layer.

Further, the outer bag for disposable body warmer packaging of the present invention may be configured such that the low air-permeability layer and the air-impermeable layer are provided on one sealant layer, and the low air-permeability portion has the low air-permeability layer, and the air-impermeable portion has the low air-permeability layer and the air-impermeable layer.

Also, the outer bag for disposable body warmer packaging of the present invention may have at least one heat-sealed portion formed by heat-sealing one or more laminated sheets, and the low air-permeability portion may be provided in at least a part of a region adjacent to the heat-sealed portion. The region adjacent to the heat-sealed portion in the outer bag for disposable body warmer packaging of the present invention refers to a portion that is in contact with the heat-sealed portion. In the outer bag for disposable body warmer packaging of the present invention, the width of the region adjacent to the heat-sealed portion starting from a point in contact with the heat-sealed portion is preferably 0.1 to 100 mm, more preferably 0.5 to 50 mm, and most preferably 1.0 to 30 mm. Also, in the outer bag for disposable body warmer packaging of the present invention, the ratio of the area of the low air-permeability portion existing in the region adjacent to the heat-sealed portion to the area of the entire low air-permeability portion existing in the outer bag for disposable body warmer packaging is preferably 1 to 50%, more preferably 3 to 50%, and most preferably 5 to 50%.

It is preferable that the first and second substrates are heat-resistant substrates. Specifically, for example, any film of various resins may be used such as a polyolefin-based resin such as a polyethylene-based resin and a polypropylene-based resin, a cyclic polyolefin-based resin, a polystyrene-based resin, an acrylonitrile-styrene copolymer (AS resin), an acrylonitrile-butadiene-styrene copolymer (ABS resin), a poly(meth)acrylic-based resin, a polycarbonate-based resin, a polyester-based resin such as polyethylene terephthalate and polyethylene naphthalate, a polyamide-based resin such as various nylons, a polyurethane-based resin, an acetal-based resin, and a cellulose-based resin. Among them, a film of a polyester-based resin, a polyolefin-based resin or a polyamide-based resin is preferable, and in particular, a film of biaxially oriented polypropylene, biaxially oriented polyethylene terephthalate or a biaxially oriented polyamide resin is preferable. Various resin films can be produced by a method where one or more of the above various resins are used and such resins are subjected singly or in combinations of two or more to multilayer co-extrusion film formation with an extrusion method, a cast molding method, a T-die method, a cutting method, an inflation method, or other film formation methods. Furthermore, various resin films can be produced by a method where two or more of the resins are used, mixed, and subjected to film formation, or the like. Further, the various resin films can be formed to be uniaxially or biaxially oriented by utilizing, for example, a tentering method or a tubular method. The thicknesses of the first and second substrates are preferably 3 to 500 µm, more preferably 5 to 300 µm, further preferably 10 to 100 µm, and most preferably 15 to 50 µm. The types of the various resins used in and/or thicknesses of the first and second substrates may be the same or different.

The low air-permeability layer is a layer which allows permeation of oxygen gas, water vapor, and hydrogen gas but has a low permeability.

As materials forming the low air-permeability layer, a homopolymer or copolymer of vinylidene chloride (which may be hereinafter generically referred to as "polyvinylidene chloride") may be preferably mentioned. Among such copolymers, a vinylidene chloride copolymer where the content of vinylidene chloride is preferably in a range from 50 to 98% by mol, more preferably in a range from 75 to 96% by mol, is preferable because of being excellent in a balance between a film formation property and gas barrier property. As the monomer copolymerizable with vinylidene chloride, specifically for example, vinyl chloride, acrylic acid esters such as methyl acrylate, ethyl acrylate, butyl acrylate, 2-ethylhexyl acrylate and 2-hydroxyethyl acrylate, methacrylic acid esters such as methyl methacrylate and glycidyl methacrylate, acrylonitrile, methacrylonitrile, and unsaturated carboxylic acids such as acrylic acid, methacrylic acid, itaconic acid, and maleic acid can be selected and used singly or in combinations of two or more. Among them, vinyl chloride or acrylic acid ester is preferably used in terms of a film formation property. The low air-permeability layer may be constituted by appropriate combinations of one type or two or more types of polyvinylidene chloride, and further by any combination where any publicly known additive such as a heat stabilizer, a light stabilizer, and a lubricant is appropriately added.

The thickness of the low air-permeability layer is not particularly limited, may be appropriately set depending on the desired oxygen gas barrier property and the like, and is preferably 0.5 to 30 µm, more preferably 0.8 to 10 µm, and most preferably 1 to 2 µm.

The polyvinylidene chloride is usually used as an emulsion or a solution. The low air-permeability portion can be formed by, for example, a method where the polyvinylidene chloride resin which is, if necessary, dissolved or dispersed in a solvent and thus formed into an application liquid is applied onto the surface of the first substrate.

The air-impermeable layer is a layer which blocks permeation of oxygen gas, water vapor, and hydrogen gas.

Metal or metal oxide may be mentioned preferably as the material for constituting the air-impermeable layer. As metals, specifically, aluminum, gold, silver, copper, nickel, chromium, germanium, selenium, titanium, tin, zinc, etc. may be mentioned. As metal oxides, specifically, aluminum oxide, silicon oxide, etc. may be mentioned. As the metal or metal oxide, aluminum, aluminum oxide, or silicon oxide is preferable in terms of economic efficiency, more preferably aluminum is preferable in terms of a gas barrier property, economic efficiency, stability and practicality.

These metal or metal oxides are vapor-deposited on the second substrate, for example, using a publicly known method such as a vacuum deposition method, a sputtering method, an ion plating method, and the like, or placing a metal foil, and thus the air-impermeable portion can be formed. The thickness of the air-impermeable layer which is a vapor-deposited film or a metal foil is preferably 50 to 5000 angstroms, more preferably 100 to 1000 angstroms, and most preferably 200 to 800 angstroms.

As the sealant layer, in general, thermal adhesive resins used in an outer bag for disposable body warmer packaging can be used without limitation. For example, low density polyethylene, medium density polyethylene, high density polyethylene, straight-chain (linear) low density polyethylene, polypropylene, an ethylene-vinyl acetate copolymer, an ionomer resin, an ethylene-ethyl acrylate copolymer, an ethylene-acrylic acid copolymer, an ethylene-methacrylic acid copolymer, an ethylene-propylene copolymer, a methylpentene polymer, and an acid-modified polyolefin-based resin where a polyolefin-based resin such as polyethylene, polystyrene or polypropylene is modified with an unsaturated carboxylic acid such as acrylic acid, methacrylic acid, maleic anhydride or fumaric acid, as well as other resins can be used singly or in combinations of two or more. Various resin films can be produced by a method where one or more of the above various resins are used and such resins are subjected singly or in combinations of two or more to multilayer co-extrusion film formation with an extrusion method, a cast molding method, a T-die method, a cutting method, an inflation method, or other film formation methods. Furthermore, various resin films can be produced by a method where two or more of the resins are used, mixed, and subjected to film formation, or the like. Further, the various resin films can be formed to be uniaxially or biaxially oriented by utilizing, for example, a tentering method or a tubular method. Among them, unoriented polypropylene, biaxially oriented polypropylene, unoriented polyethylene, low density polyethylene, medium density polyethylene, high density polyethylene or straight-chain (linear) low density polyethylene is preferable, and in particular, unoriented polypropylene, biaxially oriented polypropylene or straight-chain (linear) low density polyethylene is more preferable in terms of a thermal fusion property. The thickness of the sealant layer is preferably 5 to 300 µm, more preferably 10 to 100 µm, and most preferably 15 to 50 µm.

An adhesive layer is preferably provided between the air-impermeable layer and the low air-permeability layer so that they are laminated on the sealant layer. As the adhesive forming the adhesive layer, any adhesive usually used in the outer bag for disposable body warmer packaging can be used without any limitation, and for example, an ether-based adhesive, a polyvinyl acetate-based adhesive, polyacrylic acid ester-based adhesive made of a homopolymer of acrylic acid ethyl, butyl or 2-ethylhexyl ester, or a copolymer thereof with methyl methacrylate, acrylonitrile, styrene or the like, a cyanoacrylate-based adhesive, an ethylene copolymer-based adhesive made of a copolymer of ethylene with a monomer such as vinyl acetate, ethyl acrylate, acrylic acid or methacrylic acid, a cellulose-based adhesive, a polyester-based adhesive, a polyamide-based adhesive, a polyimide-based adhesive, an amino resin-based adhesive made of a urea resin, a melamine resin or the like, a phenol resin-based adhesive, an epoxy-based adhesive, a polyurethane-based adhesive, a reaction (meth)acrylic-based adhesive, a rubber-based adhesive made of a chloroprene rubber, a nitrile rubber, a styrene-butadiene rubber or the like, a silicone-based adhesive, an inorganic adhesive made of alkali metal silicate, low melting point glass or the like, or other adhesives can be used. The composition form of the adhesive may be any composition form such as an aqueous form, a solution form, an emulsion form, and a dispersion form. Also, the form of the adhesive may be any form such as a film-sheet form, a powder form, and a solid form. Furthermore, the adhesion mechanism may be any mechanism such as chemical reaction, solvent volatilization, thermal fusion, and thermal pressure mechanisms. Any mode usually used can be used as a usage mode of the adhesive without any limitation, and the adhesive layer can be formed by, for example, applying the adhesive onto at least one of the individual layers by a roll coating method, a gravure roll coating method, a kiss coating method, other coating methods, a printing method or the like, and then drying a solvent and the like. The content the adhesive is preferably 0.1 to 10 $g/m^2$ (dry state), more preferably 0.5 to 8 $g/m^2$ (dry state), and most preferably 1.5 to 4 $g/m^2$ (dry state).

In the outer bag for disposable body warmer packaging of the present invention, a printing ink layer may be provided as a constituent at any location. The printing ink layer can be formed by adding one or more usual ink vehicles as a main component, optionally adding, if necessary, one or two or more additives such as a plasticizer, a stabilizer, an antioxidant, a light stabilizer, an ultraviolet ray absorber, a curing agent, a crosslinking agent, a lubricant, an antistatic agent and a filler thereto, further adding a colorant such as a dye/pigment thereto, and sufficiently kneading the resultant with a solvent, a diluent or the like to prepare an ink composition; and then printing a desired character, graphic, sign, pattern, and the like with the ink composition by use of, for example, gravure printing, offset printing, relief printing, screen printing, transfer printing, flexographic printing, or other printing schemes.

Any ink vehicle usually used for the outer bag for disposable body warmer packaging can be used as the ink vehicle without any limitation, examples of which may include, flaxseed oil, tung oil, soybean oil, hydrocarbon oil, rosin, rosin ester, a rosin-modified resin, shellac, an alkyd resin, a phenol-based resin, a maleic acid resin, a natural resin, a hydrocarbon resin, a polyvinyl chloride-based resin, a polyvinyl acetate-based resin, a polystyrene-based resin, a polyvinyl butyral resin, an acrylic or methacrylic-based resin, a polyamide-based resin, a polyester-based resin, a polyurethane-based resin, an epoxy-based resin, a urea resin, a melamine resin, an amino alkyd-based resin, nitrocellulose, ethyl cellulose, a chlorinated rubber and a cyclized rubber singly or in combinations of two or more. The content of the printing ink layer is preferably 0.1 to 10 $g/m^2$ (dry state), more preferably 0.5 to 8 $g/m^2$ (dry state), and most preferably 1 to 5 $g/m^2$ (dry state).

The outer bag for disposable body warmer packaging of the present invention may further include an additional resin layer. The additional resin layer may be a layer formed from any resin as long as a gas permeation property and water vapor permeation property of the outer bag for disposable body warmer packaging of the present invention are not impaired, and can be provided at any desired position depending on the characteristics of the resin. For example, when the thermal adhesive resin which has been described above as being usable in the sealant layer is to be used in the additional resin layer, it can be provided outward against the sealant layer and function as a heat-sealed portion in formation of an outer bag. Also, when the heat-resistant resin which has been described above as being usable in the first and second substrates is to be used in the additional resin layer, it can be provided between the first and second substrates so as to enhance the strength of the multilayer film, or provided opposite to the sealant layer and at a position corresponding to the outer surface of outer bag for disposable body warmer packaging so as to function as a protection film. The thickness of the additional resin layer is not particularly limited, and is preferably 3 to 500 µm, more preferably 5 to 300 µm, further preferably 5 to 100 µm, most preferably 5 to 50 µm.

The outer bag for disposable body warmer packaging of the present invention can achieve the seal strength of preferably 15.0 N/15 mm or larger, more preferably 20.0 N/15 mm or larger, and most preferably 25.0 N/15 mm or larger. By defining the seal strength of the outer bag for disposable body warmer packaging of the present invention within the above-identified numerical ranges, it is made possible to achieve the effect that the outer bag is not easily opened or broken even when a large impact acts upon the outer bag from outside.

[First Embodiment]

In the first embodiment, the low air-permeability portion has a first substrate and a low air-permeability layer laminated on the first substrate. The air-impermeable portion has a second substrate and an air-impermeable layer laminated on the second substrate. Those that have been described above can be used without any limitation as the substrate, the low air-permeability layer and the air-impermeable layer as well as the sealant layer and the like.

The features of the outer bag for disposable body warmer packaging of the first embodiment will be described with reference to FIGS. 1A to 1C.

FIG. 1A is a cross-sectional view. FIG. 1B(a) is a plan view where the outer bag is viewed in the direction of an arrow X1 in FIG. 1A. FIG. 1B(b) is a plan view where the outer bag is viewed in the direction of an arrow Y1 in FIG. 1A. FIG. 1C is a cross-sectional view illustrating a laminated state in the heat-sealed portion indicated by C1 in FIG. 1A.

In the first embodiment, according to the outer bag for disposable body warmer packaging of the present invention, the first multilayer film A1 laminated on the first sealant layer 30a and the second multilayer film B1 laminated on the second sealant layer 30b are stacked each other. The peripheral portion thereof is four-side sealed, and thus the bag can be formed. The space inside of the bag becomes the accommodating portion of the disposable body warmer.

Figure 1B:
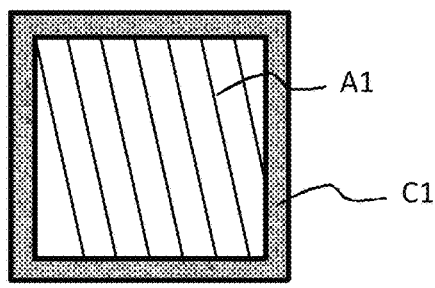
FIG. 1B is a plan view of the outer bag for disposable body warmer packaging in the Embodiment 1 of the present invention, where (a) is a plan view where the outer bag is viewed in the direction of an arrow X1 in FIG. 1A and (b) is a plan view where the outer bag is viewed in the direction of an arrow Y1 in FIG. 1A.
Figure 1B:
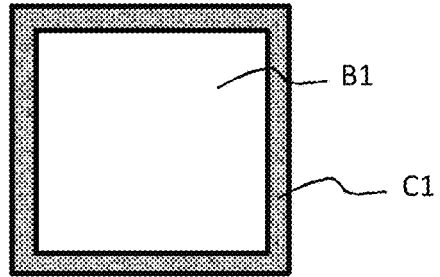
Figure 1C:
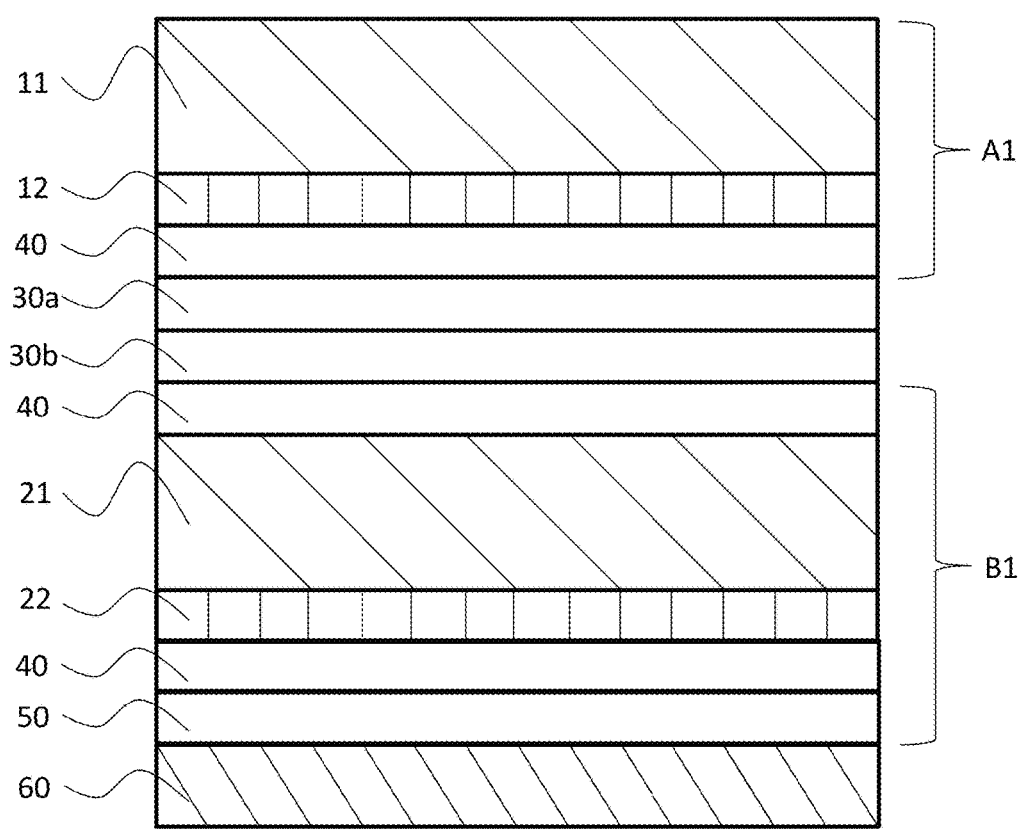
FIG. 1C is an explanatory view illustrating a layered structure of a cross section of a heat-sealed portion (C1 in FIG. 1A) of the outer bag for disposable body warmer packaging in the Embodiment 1 of the present invention.

FIG. 1C illustrates the layered structure of the first multilayer film A1 and the second multilayer film B1 in the heat-sealed portion C1. In FIG. 1C, the first multilayer film A1 and the second multilayer film B1 are laminated in a state where the first sealant layer 30a and the second sealant layer 30b are face-to face with each other. When viewed from the lower layer's side in FIG. 1C, the second multilayer film B1 is laminated on the additional resin layer 60. The first multilayer film A1 is laminated on the first and second sealant layers 30a and 30b stacked on the second multilayer film B1. The second multilayer film B1 is obtained by laminating, starting from the lower layer's side, the printing ink layer 50, the adhesive layer 40, the vapor-deposited layer 22, the second heat-resistant resin substrate 21, and the adhesive layer 40. The first multilayer film A1 is obtained by laminating, starting from the lower layer's side, the adhesive layer 40, the polyvinylidene chloride layer 12, and the first heat-resistant resin substrate 11. The portion where the second multilayer film B1 is laminated becomes the air-impermeable portion. The second multilayer film B1 includes the vapor-deposited layer (air-impermeable layer) 22 obtained by vapor deposition on the second heat-resistant resin substrate 21. The portion where the first multilayer film A1 is laminated becomes the low air-permeability portion. The first multilayer film A1 includes the polyvinylidene chloride layer (low air-permeability layer) 12 laminated on the first heat-resistant resin substrate 11. The "ratio of the area of the low air-permeability portion to the total internal area of the accommodating portion" refers to a ratio of the area of the low air-permeability portion to the area of the inside of the bag except for the heat-sealed portion. In the first embodiment, since the first multilayer film A1 and the second multilayer film B1 constitute the front side and the back side of the bag, respectively, the ratio of the area of the low air-permeability portion to the total internal area of the accommodating portion is 50%.

[Second Embodiment]

The second embodiment is a modified example of the first embodiment. In the same manner as in the first embodiment, the low air-permeability portion includes a first substrate and a low air-permeability layer laminated on the first substrate. The air-impermeable portion has a second substrate and an air-impermeable layer laminated on the second substrate. Those that have been described above can be used without any limitation as the substrate, the low air-permeability layer, and the air-impermeable layer as well as the sealant layer and the like.

The features of the outer bag for disposable body warmer packaging of the second embodiment will be described with reference to FIGS. 2A to 2C.

Figure 2A:
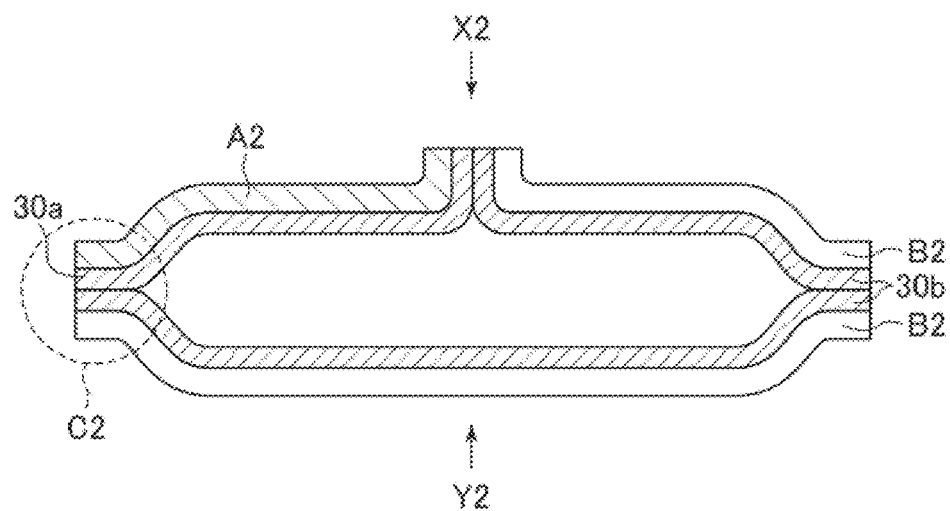
FIG. 2A is a cross-sectional view of an outer bag for disposable body warmer packaging in Embodiment 2 of the present invention.

FIG. 2A is a cross-sectional view. FIG. 2B(a) is a plan view where the outer bag is viewed in the direction of an arrow X2 in FIG. 2A. FIG. 2B(b) is a plan view where the outer bag is viewed in the direction of an arrow Y2 in FIG. 2A. FIG. 2C is a cross-sectional view illustrating a laminated state in the heat-sealed portion indicated by C2 in FIG. 2A.

In the second embodiment, according to the outer bag for disposable body warmer packaging of the present invention, one end of the first multilayer film A2 laminated on the first sealant layer 30a and the one end of the second multilayer film B2 laminated on the second sealant layer 30b are partly stacked each other to be heat-sealed. Thereby, the laminated sheet on the front side of the bag (the side viewed in the direction indicated by the arrow X2 in FIG. 2A) is formed such that the low air-permeability portion of the first multilayer film A2 and the air-impermeable portion of the second multilayer film B2 are adjacently positioned. The laminated sheet on the back side of the bag (the side viewed in the direction Y2 of FIG. 2A) is formed by the second multilayer film B2 laminated on the second sealant layer 30b. In addition, the bag can be formed by stacking the laminated sheets on the front side and the back side of the bag each other and four-side sealing a peripheral portion thereof. The space inside of the bag becomes the accommodating portion of the disposable body warmer.

Figure 2B:
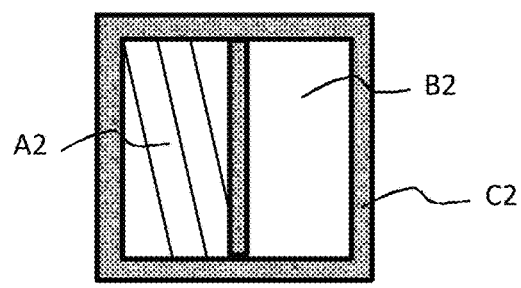
FIG. 2B is a plan view of the outer bag for disposable body warmer packaging in the Embodiment 2 of the present invention, where (a) is a plan view where the outer bag is viewed in the direction of an arrow X2 in FIG. 2A and (b) is a plan view where the outer bag is viewed in the direction of an arrow Y2 in FIG. 2A.
Figure 2B:
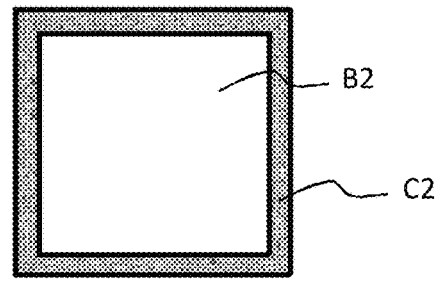
Figure 2C:
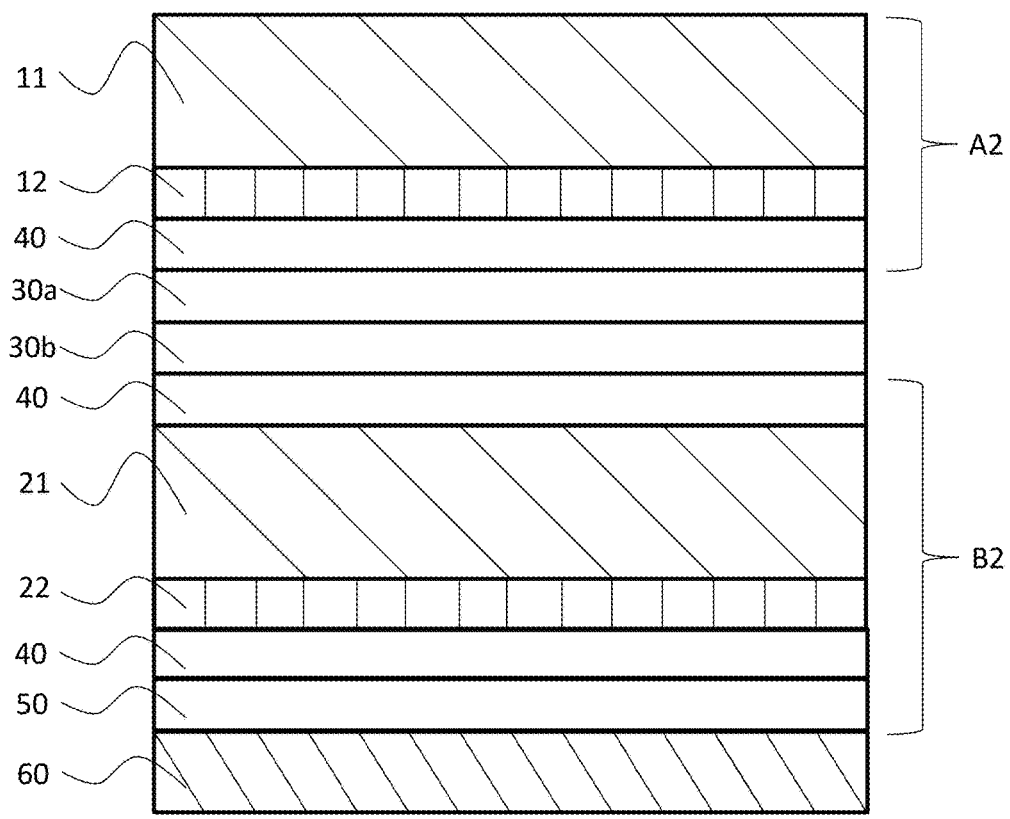
FIG. 2C is an explanatory view of a layered structure of a cross section of a heat-sealed portion (C2 in FIG. 2A) of the outer bag for disposable body warmer packaging in the Embodiment 2 of the present invention.

FIG. 2C illustrates a layered structure of the first multilayer film A2 and the second multilayer film B2 in the heat-sealed portion C2. In FIG. 2C, the same layered structure as that in FIG. 1C of the first embodiment is provided. The portion where the second multilayer film B2 is laminated becomes the air-impermeable portion. The second multilayer film B2 includes a vapor-deposited layer (air-impermeable layer) 22 obtained by vapor deposition on the second heat-resistant resin substrate 21. The portion where the first multilayer film A2 is laminated becomes the low air-permeability portion. The first multilayer film A2 includes a polyvinylidene chloride layer (low air-permeability layer) 12 laminated on the first heat-resistant resin substrate 11. In the second embodiment, the front side of the bag is constituted by the first multilayer film A2 and the second multilayer film B2 each having the ratio of the area of 50%. The back side of the bag is constituted by the second multilayer film B2. Thereby, the ratio of the area of the low air-permeability portion to the total internal area of the accommodating portion is 25%.

Figure 2D:
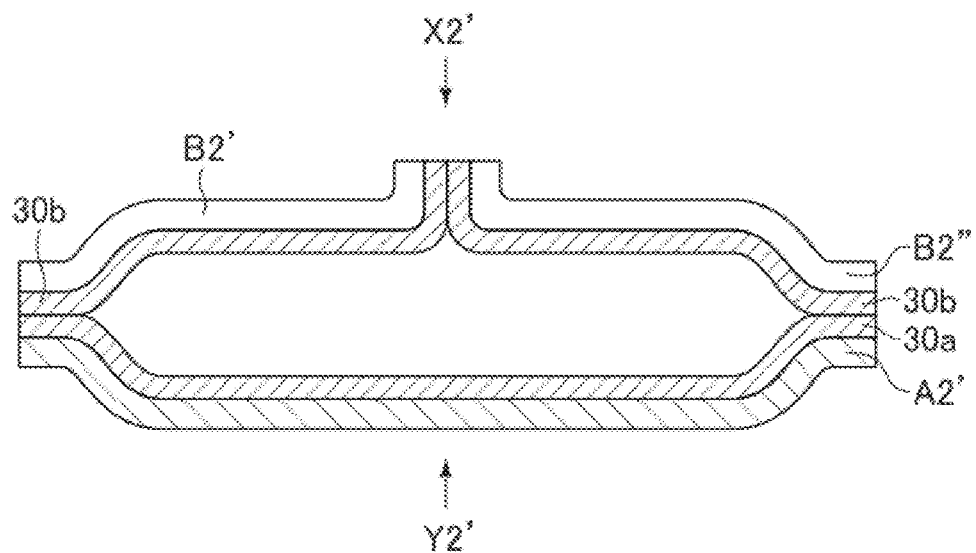
FIG. 2D is a cross-sectional view of the outer bag for disposable body warmer packaging in the modified example of the Embodiment 2 of the present invention.

Also, FIG. 2D illustrates a modified example of the second embodiment. FIG. 2D is a cross-sectional view.

In the modified example of the second embodiment, according to the outer bag for disposable body warmer packaging of the present invention, one end of the second multilayer film B2' laminated on the second sealant layer 30b and the one end of the second multilayer film B2" laminated on the second sealant layer 30b are partly stacked each other so as to be heat-sealed. Thus, the laminated sheet on the front side of the bag (the side viewed in the direction indicated by an arrow X2' of FIG. 2D) is formed such that the air-impermeable portion of the second multilayer film B2' and the air-impermeable portion of the second multilayer film B2" are adjacently positioned. The laminated sheet on the back side of the bag (the side viewed in the direction indicated by an arrow Y2' of FIG. 2D) is formed by the first multilayer film A2' laminated on the first sealant layer 30a. In addition, the laminated sheets on the front side and the back side of the bag are stacked each other. A peripheral portion thereof is four-side sealed, and thus the bag can be formed. The space inside of the bag becomes the accommodating portion of the disposable body warmer.

In the modified example of the second embodiment, the front side of the bag is constituted by the second multilayer film B2' and the second multilayer film B2" each having the ratio of the area of 50%. The back side of the bag is constituted by the first multilayer film A2'. Thereby, the ratio of the area of the low air-permeability portion to the total internal area of the accommodating portion is 50%.

[Third Embodiment]

In the third embodiment, the low air-permeability layer and the air-impermeable layer are provided on one substrate. The low air-permeability portion has the substrate and the low air-permeability layer. The air-impermeable portion has the substrate and the air-impermeable layer. Those that have been described above can be used without any limitation as the substrate, the low air-permeability layer and the air-impermeable layer, the sealant layer, and the others or the like.

Figure 3A:
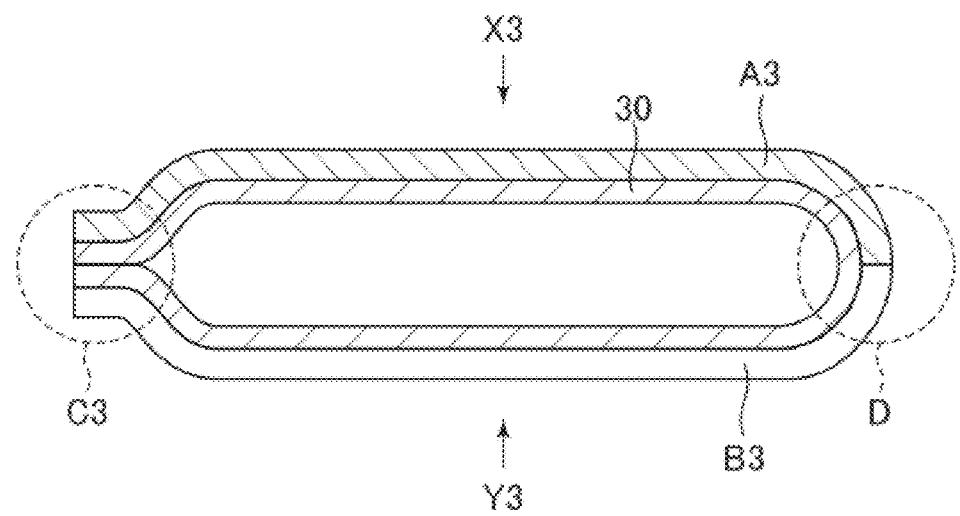
FIG. 3A is a cross-sectional view of an outer bag for disposable body warmer packaging of Embodiment 3 of the present invention.
Figure 3B:
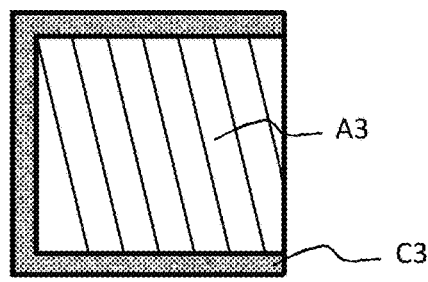
FIG. 3B is a plan view of the outer bag for disposable body warmer packaging in the Embodiment 3 of the present invention, where (a) is a plan view where the outer bag is viewed in the direction of an arrow X3 in FIG. 3A and (b) is a plan view where the outer bag is viewed in the direction of an arrow Y3 in FIG. 3A.
Figure 3B:
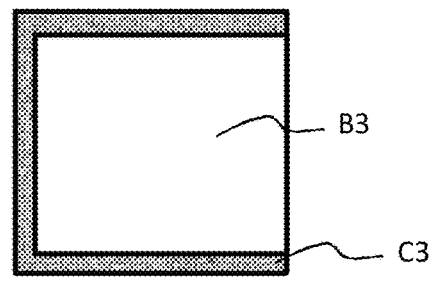
Figure 3C:
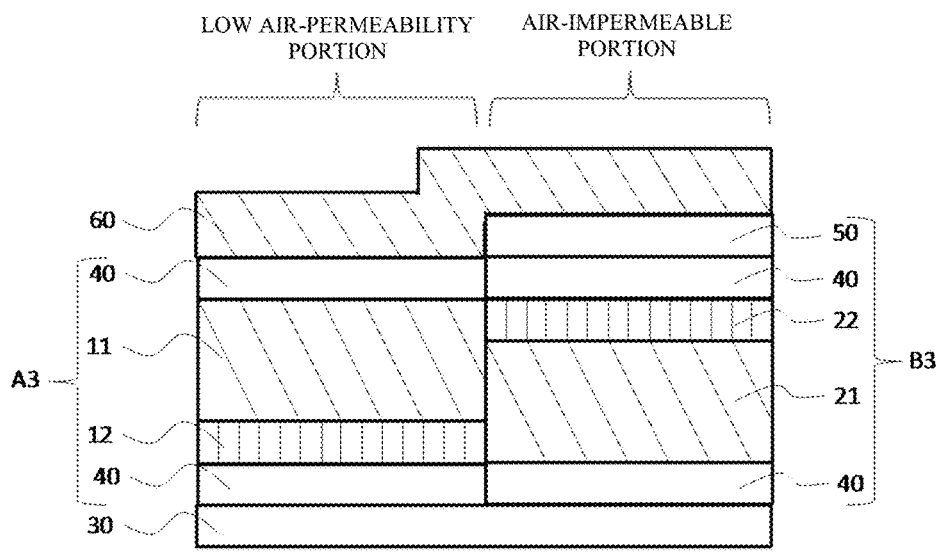
FIG. 3C is an explanatory view of a layered structure of a cross section of a connected portion (D in FIG. 3A) of the outer bag for disposable body warmer packaging in the Embodiment 3 of the present invention.
Figure 3D:
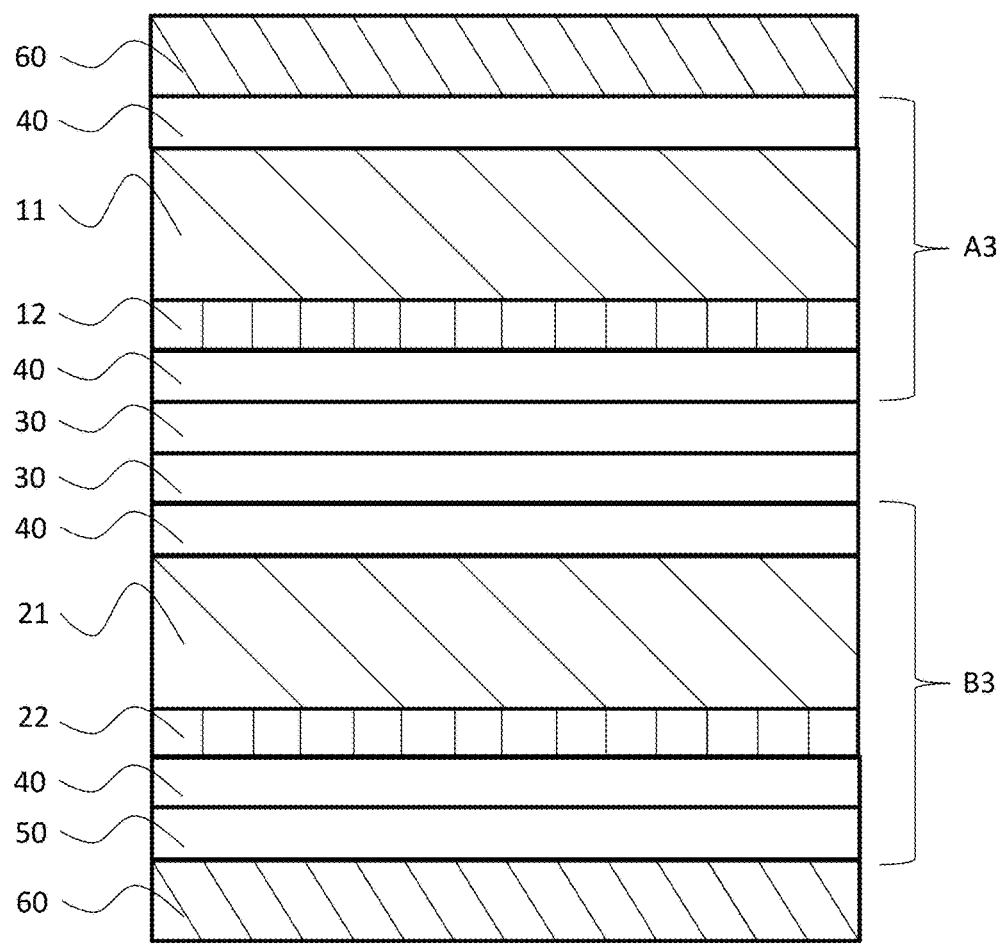
FIG. 3D is an explanatory view of a layered structure of a cross section of a heat-sealed portion (C3 in FIG. 3A) of the outer bag for disposable body warmer packaging in the Embodiment 3 of the present invention.

The features of the outer bag for disposable body warmer packaging according to the third embodiment will be described with reference to FIGS. 3A to 3D. FIG. 3A is a cross-sectional view. FIG. 3B(a) is a plan view where the outer bag is viewed in the direction of an arrow X3 in FIG. 3A. FIG. 3B(b) is a plan view where the outer bag is viewed in the direction of an arrow Y3 in FIG. 3A. FIG. 3C is a cross-sectional view illustrating the laminated state in the connected portion indicated by D in FIG. 3A. FIG. 3D is a cross-sectional view illustrating the laminated state in the heat-sealed portion indicated by C3 in FIG. 3A.

In the third embodiment, according to the outer bag for disposable body warmer packaging of the present invention, the first multilayer film A3 and the second multilayer film B3 are joined on one sealant layer 30 by the connected portion D. The three peripheral portions thereof are three-side sealed, and thus the bag can be formed. The space in the bag becomes the accommodating portion of the disposable body warmer. The heat-sealed portion C3 includes the first multilayer film A3 and the second multilayer film B3.

With regard to the connected portion D, when viewed from the lower layer's side in FIG. 3C, the first multilayer film A3 and the second multilayer film B3 are adjacently laminated on the common sealant layer 30. A common additional resin layer 60 is laminated on the first multilayer film A3 and the second multilayer film B3, and thus the laminated sheet is constituted. The first multilayer film A3 is constituted by laminating, starting from the lower layer, the adhesive layer 40, the polyvinylidene chloride layer 12, the first heat-resistant resin substrate 11, and the adhesive layer 40. The second multilayer film B3 is constituted by laminating, starting from the lower layer, the adhesive layer 40, the second heat-resistant resin substrate 21, the vapor-deposited layer 22, the adhesive layer 40, and the printing ink layer 50.

The heat-sealed portion C3 is constituted by laminating, when viewed from the lower layer of FIG. 3D, the second multilayer film B3, two respective sealant layers 30, and the first multilayer film A3 on the additional resin layer 60. The second multilayer film B3 is constituted by laminating, starting from the lower layer, the printing ink layer 50, the adhesive layer 40, the vapor-deposited layer 22, the second heat-resistant resin substrate 21, and the adhesive layer 40. The first multilayer seal A3 is constituted by laminating, starting from the lower layer, an adhesive layer 40, the polyvinylidene chloride layer 12, the first heat-resistant resin substrate 11, and an adhesive layer 40.

The portion where the second multilayer film B3 is laminated becomes the air-impermeable portion. The second multilayer film B3 includes vapor-deposited layer (air-impermeable layer) 22 obtained by vapor deposition on the second heat-resistant resin substrate 21. The portion where the first multilayer film A3 is laminated becomes the low air-permeability portion. The first multilayer film A3 includes the polyvinylidene chloride layer (low air-permeability layer) 12 laminated on the first heat-resistant resin substrate 11. In the third embodiment, the first multilayer film A3 and the second multilayer film 133 constitute the front side and the back side of the bag, respectively. Thereby, the ratio of the area of the low air-permeability portion to the total internal area of the accommodating portion is 50%.

[Fourth Embodiment]

In the fourth embodiment, the low air-permeability layer and the air-impermeable layer are provided on one sealant layer. The low air-permeability portion has the low air-permeability layer. The air-impermeable portion has the low air-permeability layer and the air-impermeable layer. Those that have been described above can be used without any limitation as the substrate, the low air-permeability layer and the air-impermeable layer as well as the sealant layer and the like. In the fourth embodiment, the portion where the low air-permeability layer and the air-impermeable layer are laminated constitutes the air-impermeable portion. The portion where the air-impermeable layer is not laminated constitutes the low air-permeability portion.

The features of the outer bag for disposable body warmer packaging according to the fourth embodiment will be described with reference to FIGS. 4A to 4C.

Figure 4A:
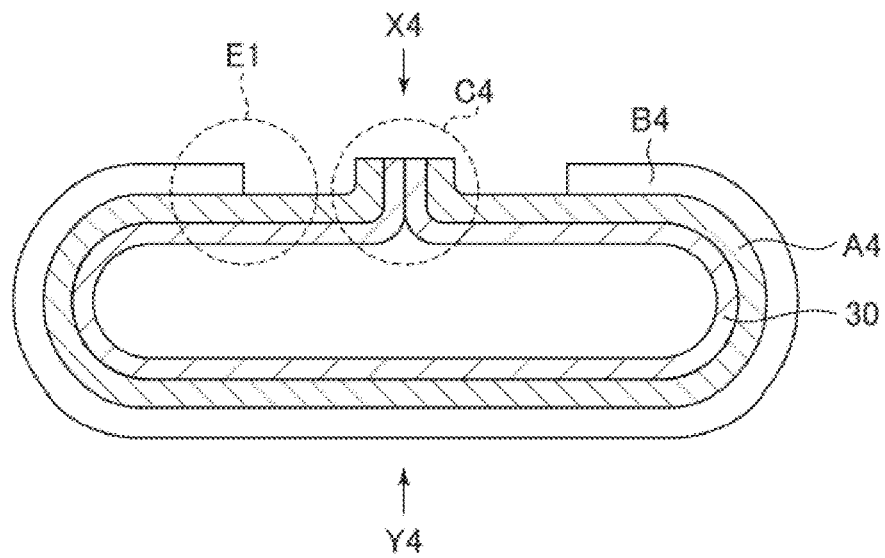
FIG. 4A is a cross-sectional view of an outer bag for disposable body warmer packaging in Embodiment 4 of the present invention.
Figure 4B:
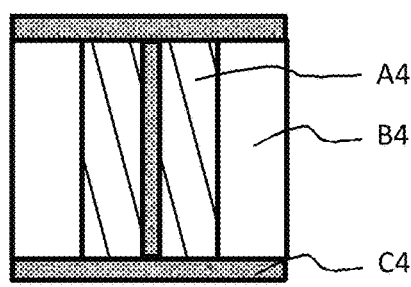
FIG. 4B is a plan view of the outer bag for disposable body warmer packaging in the Embodiment 4 of the present invention, where (a) is a plan view where the outer bag is viewed in the direction of an arrow X4 in FIG. 4A and (b) is a plan view where the outer bag is viewed in the direction of an arrow Y4 in FIG. 4A.
Figure 4B:
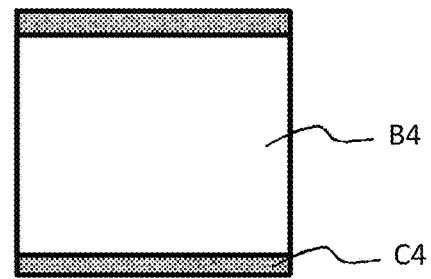

FIG. 4A is a cross-sectional view. FIG. 4B(a) is a plan view where the outer bag is viewed in the direction of an arrow X4 in FIG. 4A. FIG. 4B(b) is a plan view where the outer bag is viewed in the direction of an arrow Y4 in FIG. 4A. FIG. 4C is a cross-sectional view illustrating the laminated state in the layered portion indicated by E1 in FIG. 4A.

In the fourth embodiment, a laminated sheet is formed by laminating the first multilayer film A4 on one sealant layer 30 over the entire area of the sealant layer 30 and laminating the second multilayer film B4 on a region except for the peripheral portion of the first multilayer film A4. The laminated sheet is wound such that the sealant layer 30 becomes the inner surface's side of the outer bag and the second multilayer film B4 becomes the outer surface's side of the outer bag. The peripheral portion of the laminated sheet is three-side pillow-sealed, and thus the bag can be formed. The space in the bag becomes the accommodating portion of the disposable body warmer. Both ends of the laminated sheet do not include the second multilayer film B4.

In FIG. 4A, the heat-sealed portion is indicated by C4.

Figure 4C:
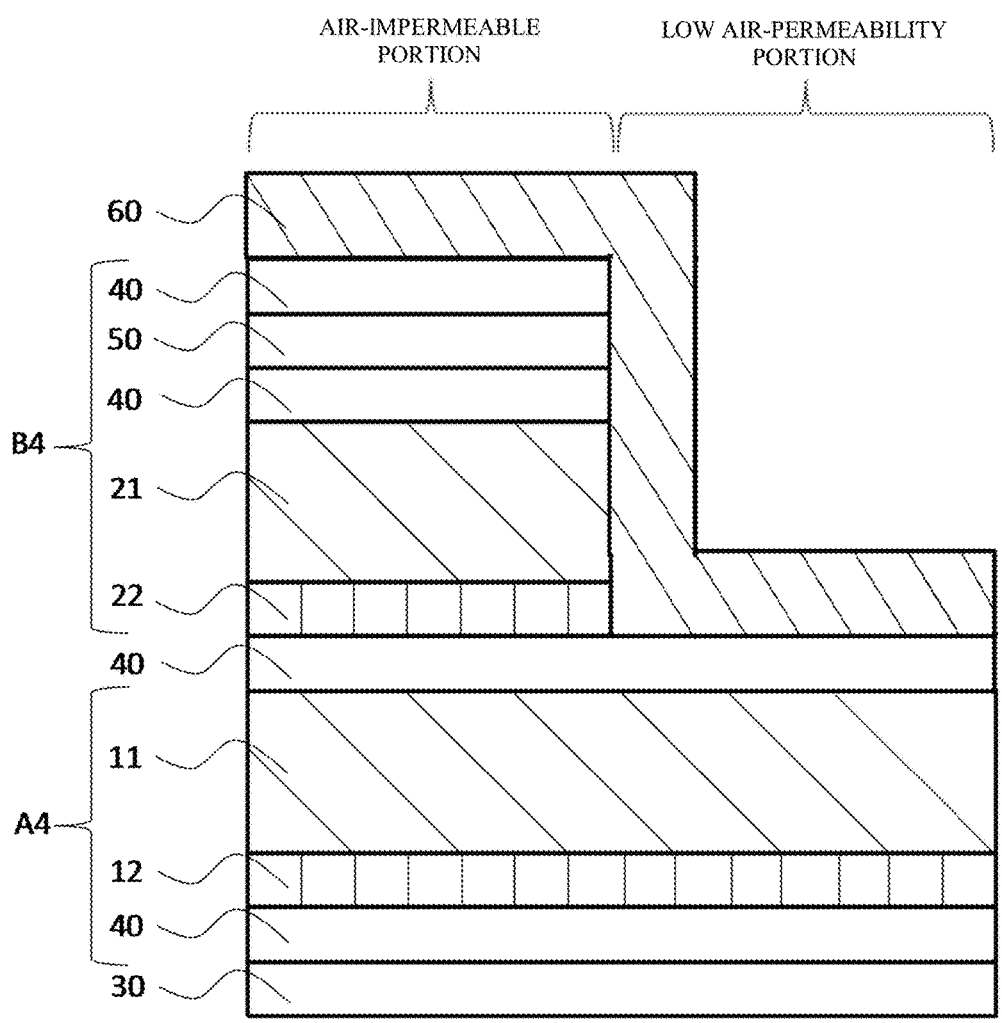
FIG. 4C is an explanatory view illustrating a layered structure of a cross section of a layered portion (E1 in FIG. 3A) of the outer bag for disposable body warmer packaging in the Embodiment 4 of the present invention.

FIG. 4C illustrates the layered structure of the first multilayer film A4 and the second multilayer film B4 in the layered portion E1 illustrated in FIG. 4A. The portion where the second multilayer film B4 is laminated on the first multilayer film A4 laminated on the sealant layer 30 becomes the air-impermeable portion. The portion where only the first multilayer film A4 resides and the second multilayer film B4 is not laminated becomes the low air-permeability portion. The air-impermeable portion is obtained by laminating, an additional resin layer 60, an adhesive layer 40, a printing ink layer 50, an adhesive layer 40, a second heat-resistant resin substrate 21, a vapor-deposited layer (air-impermeable layer) 22, an adhesive layer 40, a first heat-resistant resin substrate 11, a polyvinylidene chloride layer (low air-permeability layer) 12, an adhesive layer 40, and a sealant layer 30 when viewed from the outer surface's side of the outer bag. The low air-permeability portion is obtained by laminating an additional resin layer 60, an adhesive layer 40, a first heat-resistant resin substrate 11, a polyvinylidene chloride layer (low air-permeability layer) 12, an adhesive layer 40, and a sealant layer 30 when viewed from the outer surface's side of the outer bag. Depending on the cases, a printing ink layer 50, an adhesive layer 40, and an additional resin layer 60 may be further laminated on the first heat-resistant resin substrate 11. The area of the low air-permeability portion can be adjusted by changing the area where the second multilayer film B4 is laminated. In FIGS. 4A to 4C, the second multilayer film B4 is laminated on the most part of the area of the first multilayer film A4 except for both ends thereof. The ratio of the area of the low air-permeability portion to the total internal area of the accommodating portion is 15%.

[Fifth Embodiment]

The fifth embodiment is a modified example of the fourth embodiment. In the same manner as in the fourth embodiment, the low air-permeability layer and the air-impermeable layer are provided on one sealant layer 30. The low air-permeability portion has the low air-permeability layer. The air-impermeable portion has the low air-permeability layer and the air-impermeable layer. Those that have been described above can be used without any limitation as the substrate, the low air-permeability layer and the air-impermeable layer, the sealant layer 30, and the like. In the fifth embodiment, the portion where the low air-permeability layer and the air-impermeable layer are laminated on the one sealant layer constitutes the air-impermeable portion. The portion where the air-impermeable layer is not laminated constitutes the low air-permeability portion.

The features of the outer bag for disposable body warmer packaging according to the fifth embodiment will be described with reference to FIGS. 5A to 5C.

Figure 5A:
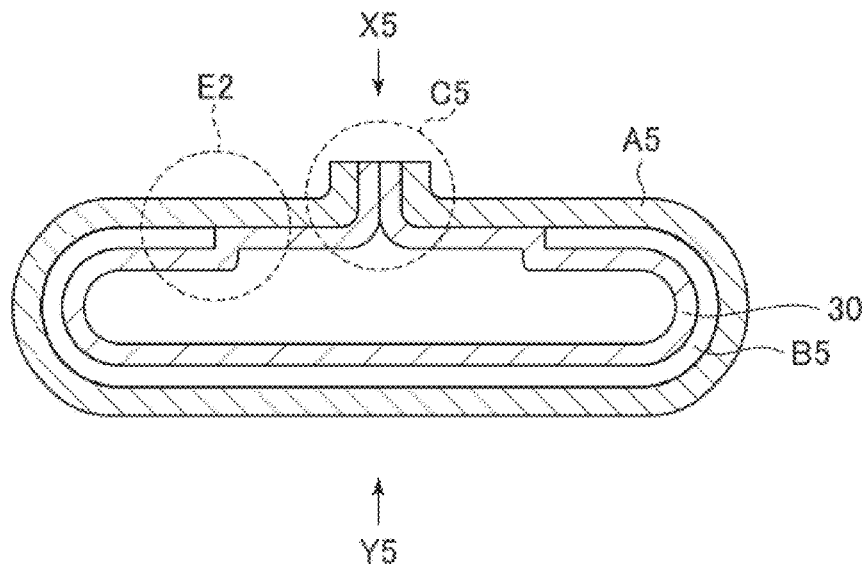
FIG. 5A is a cross-sectional view of the outer bag for disposable body warmer packaging in the Embodiment 5 of the present invention.
Figure 5B:
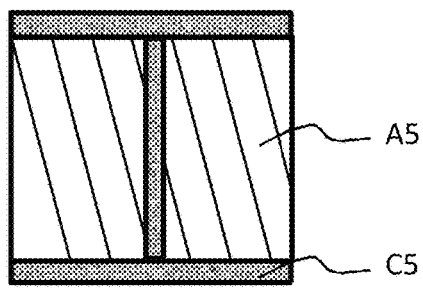
FIG. 5B is a plan view of the outer bag for disposable body warmer packaging in the Embodiment 5 of the present invention, where (a) is a plan view where the outer bag is viewed in the direction of an arrow X5 in FIG. 5A and (b) is a plan view where the outer bag is viewed in the direction of an arrow Y5 in FIG. 5A.
Figure 5B:
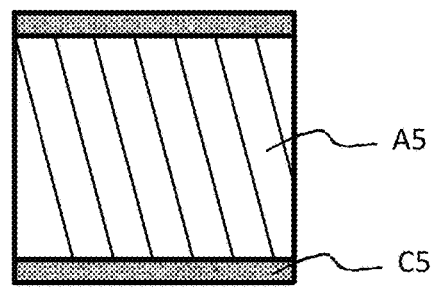

FIG. 5A is a cross-sectional view. FIG. 5B(a) is a plan view where the outer bag is viewed in the direction of an arrow X5 in FIG. 5A. FIG. 5B(b) is a plan view where the outer bag is viewed in the direction of an arrow Y5 in FIG. 5A. FIG. 5C is a cross-sectional view illustrating a laminated state in the layered portion indicated by E2 in FIG. 5A.

In the fifth embodiment, a laminated sheet is formed by laminating the second multilayer film B5 on a region of the sealant layer 30 except for the peripheral portion of the sealant layer 30 and laminating the first multilayer film A5 having the same size as the entire area of the sealant layer 30 on the second multilayer film B5 and the sealant layer 30. The laminated sheet is wound such that the first multilayer film A5 becomes the outer surface's side of the outer bag and the sealant layer 30 becomes the inner surface's side of the outer bag. The peripheral portion of the laminated sheet is three-side pillow-sealed, and thus the bag thus can be formed. The space in the bag becomes the accommodating portion of the disposable body warmer. Both ends of the laminated sheet does not include the second multilayer film B5.

In FIG. 5A, the heat-sealed portion is indicated by C5.

Figure 5C:
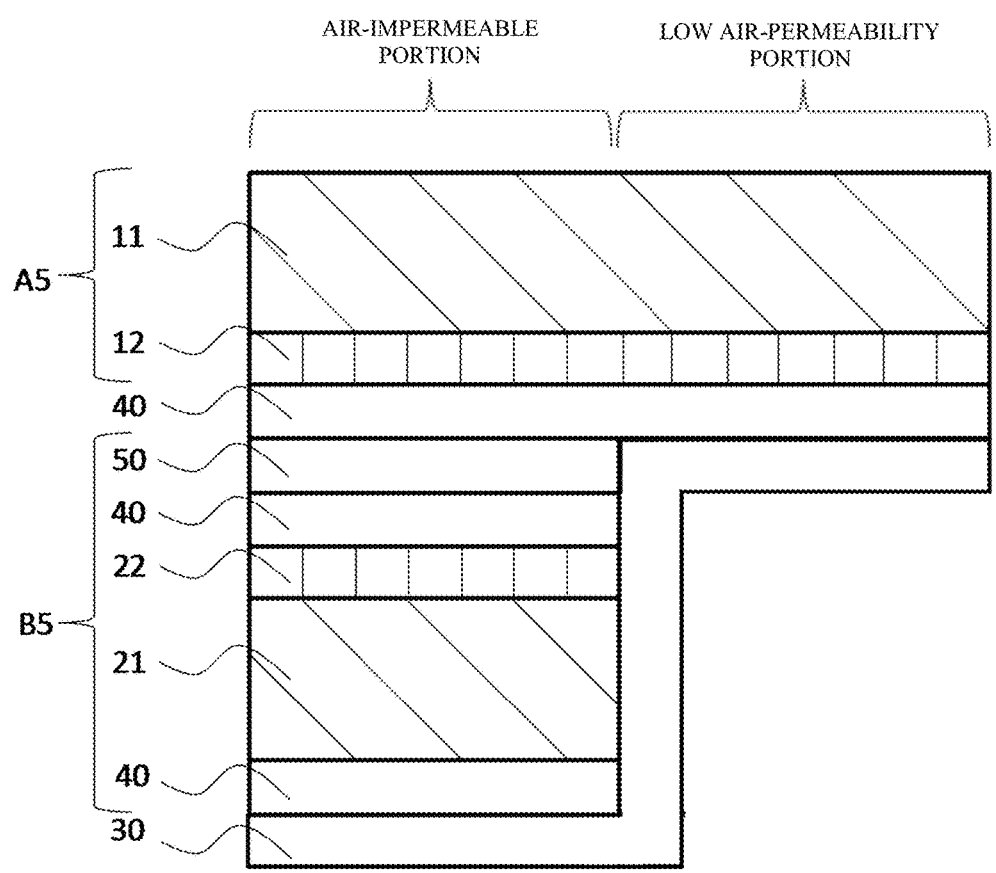
FIG. 5C is an explanatory view illustrating a layered structure of a cross section of a layered portion (E2 in FIG. 5A) of the outer bag for disposable body warmer packaging in the Embodiment 5 of the present invention.

FIG. 5C illustrates a layered structure of the first multilayer film A5 and the second multilayer film B5 in the layered portion E2 indicated in FIG. 5A. The second multilayer film B5 is laminated on a region except for both ends and their neighborhood of the sealant layer 30 The first multilayer film A5 is laminated by the same area as that of the sealant layer 30 on the second multilayer film B5 and the sealant layer 30. The portion where the first multilayer film A5 and the second multilayer film B5 are laminated becomes the air-impermeable portion. The portion where the second multilayer film B5 is not laminated becomes the low air-permeability portion. As illustrated in FIG. 5C, the air-impermeable portion is constituted by laminating, when viewed from the outer surface's side of the outer bag, the first heat-resistant resin substrate 11, the polyvinylidene chloride layer (low air-permeability layer) 12, the adhesive layer 40, the printing ink layer 50, the adhesive layer 40, the vapor-deposited layer (air-impermeable layer) 22, the second heat-resistant resin substrate 21, the adhesive layer 40, and the sealant layer 30. The low air-permeability portion is constituted by laminating, when viewed from the outer surface's side of the outer bag, the first heat-resistant resin substrate 11, the polyvinylidene chloride layer (low air-permeability layer) 12, and the sealant layer 30. Depending on the cases, the low air-permeability portion may be configured such that an adhesive layer 40, a printing ink layer 50, and an adhesive layer 40 are further provided between the polyvinylidene chloride layer 12 and the sealant layer 30. The area of the low air-permeability portion can be adjusted by changing the area where the second multilayer film B5 is laminated. In FIGS. 5A to 5C, the second multilayer film B5 is laminated on the most part of the region except for both ends and their neighborhood of the sealant layer 30. The ratio of the area of the low air-permeability portion to the total internal area of the accommodating portion is 15%.

[Sixth Embodiment]

The sixth embodiment is a modified example of the fourth embodiment. In the same manner as in the fourth embodiment, the low air-permeability layer and the air-impermeable layer are provided on one sealant layer 30. The low air-permeability portion has the low air-permeability layer. The air-impermeable portion has the low air-permeability layer and the air-impermeable layer. Those that have been described above can be used without any limitation as the substrate, the low air-permeability layer and the air-impermeable layer, the sealant layer, and the like. In the sixth embodiment, one laminated sheet is wound and stacked each other and the peripheral portion thereof is three-side sealed. The portion where the low air-permeability layer and the air-impermeable layer are laminated constitutes the air-impermeable portion. The portion where the air-impermeable layer is not laminated constitutes the low air-permeability portion.

The features of the outer bag for disposable body warmer packaging according to the sixth embodiment will be described with reference to FIGS. 6A to 6C.

Figure 6A:
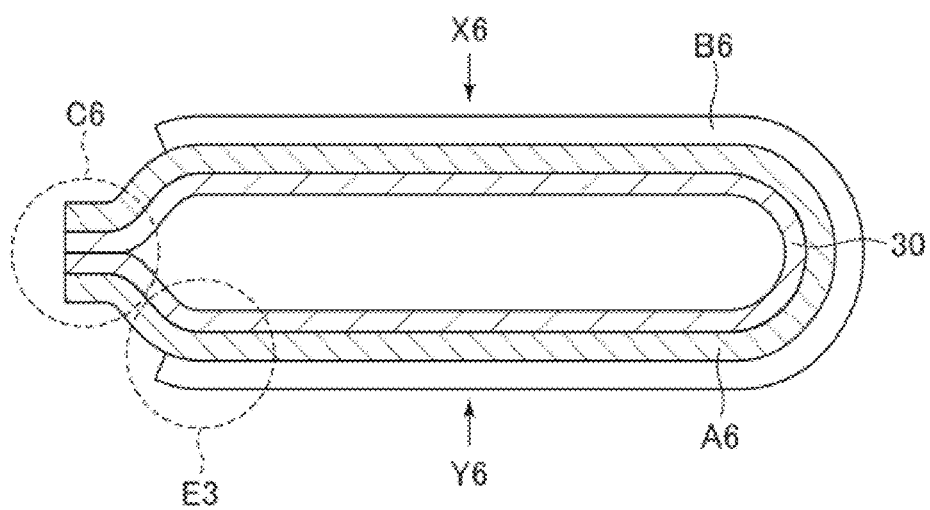
FIG. 6A is a cross-sectional view of an outer bag for disposable body warmer packaging in the Embodiment 6 of the present invention.

FIG. 6A is a cross-sectional view. FIG. 6B(a) is a plan view where the outer bag is viewed in the direction of an arrow X6 in FIG. 6A. FIG. 6B(b) is a plan view where the outer bag is viewed in the direction of an arrow Y6 in FIG. 6A. FIG. 6C is a cross-sectional view illustrating a laminated state in the layered portion of a region including the neighborhood of the heat-sealed portion indicated by E3 in FIG. 6A.

In the sixth embodiment, a laminated sheet is formed by laminating the first multilayer film A6 on the sealant layer 30 over the entire area of the sealant layer 30 and laminating the second multilayer film B6 in a region except for the peripheral portion of the first multilayer film A6. The laminated sheet is wound such that the sealant layer 30 is on the inner surface's side of the outer bag and the second multilayer film B6 is on the outer surface's side of the outer bag. Both ends of the laminated sheet are stacked each other. The peripheral portion thereof is three-side sealed, and thus a bag can be formed. The space in the bag becomes the accommodating portion of the disposable body warmer. Both ends of the laminated sheet does not include the second multilayer film B6.

In FIG. 6A, the heat-sealed portion is indicated by C6.

Figure 6B:
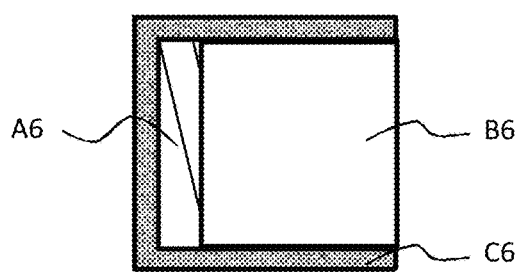
FIG. 6B is a plan view of the outer bag for disposable body warmer packaging in the Embodiment 6 of the present invention, where (a) is a plan view where the outer bag is viewed in the direction of an arrow X6 in FIG. 6A and (b) is a plan view where the outer bag is viewed in the direction of an arrow Y6 in FIG. 6A.
Figure 6B:
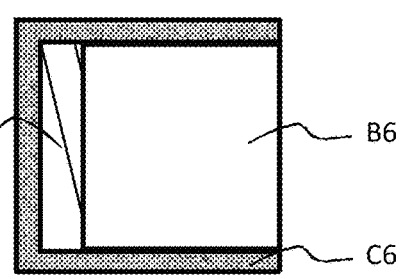
Figure 6C:
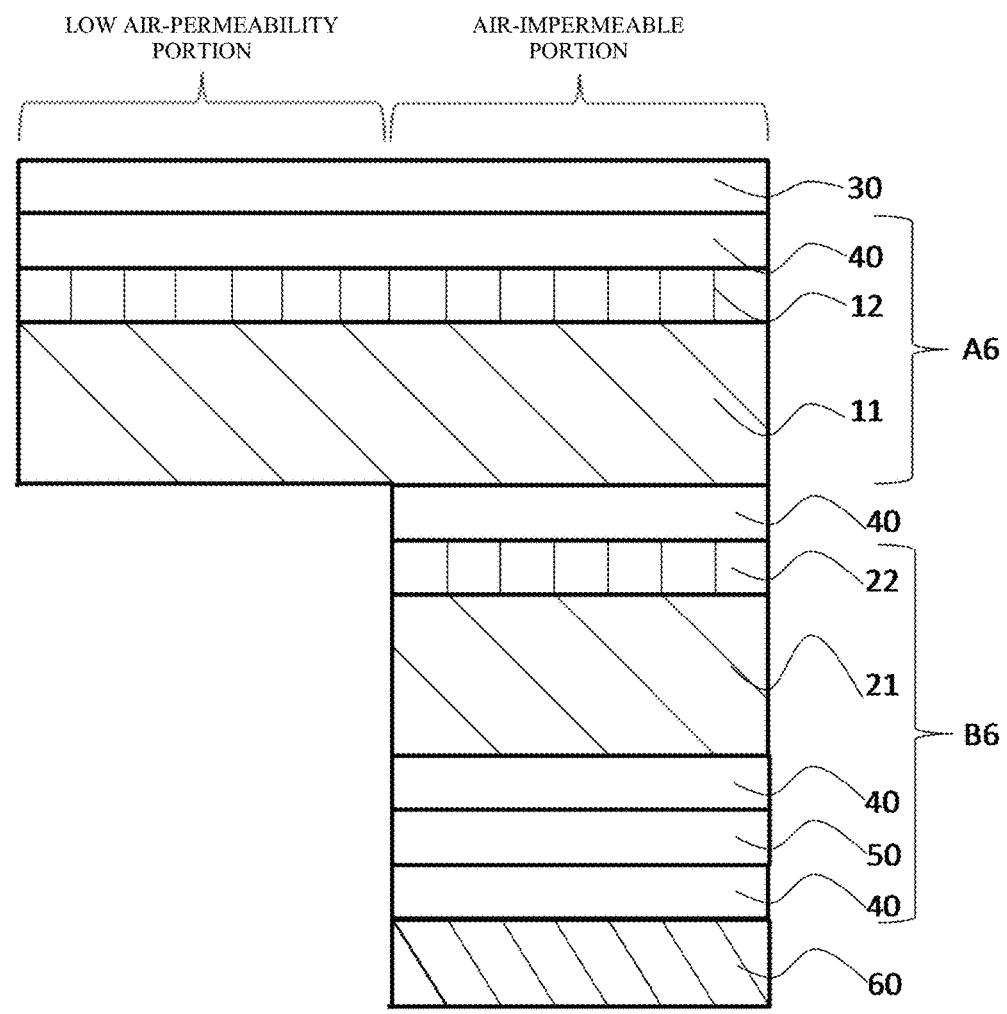
FIG. 6C is an explanatory view illustrating a layered structure of a cross section of layered portion (E3 in FIG. 6A) of the outer bag for disposable body warmer packaging in the Embodiment 6 of the present invention.

FIG. 6C illustrates the layered structure of a cross section of the layered portion E3 in the neighborhood of the heat-sealed portion illustrated in FIG. 6A. In FIG. 6C, the air-impermeable portion is constituted by laminating, when viewed from the outer surface's side of the outer bag, the additional resin layer 60, the adhesive layer 40, the printing ink layer 50, the adhesive layer 40, the second heat-resistant resin substrate 21, the vapor-deposited layer (air-impermeable layer) 22, the adhesive layer 40, the first heat-resistant resin substrate 11, the polyvinylidene chloride layer (low air-permeability layer) 12, the adhesive layer 40, and the sealant layer 30. In FIG. 6C, the low air-permeability portion adjacent to the heat-sealed portion of the laminated sheet is constituted by laminating, when viewed from the outer surface's side of the outer bag, the first heat-resistant resin substrate 11, the polyvinylidene chloride layer (low air-permeability layer) 12, the adhesive layer 40, and the sealant layer 30. In the low air-permeability portion, an adhesive layer 40, a printing ink layer 50, an adhesive layer 40, and an additional resin layer 60 may be further laminated on the outer side of the first heat-resistant resin layer 11.

The area of the low air-permeability portion can be adjusted by changing the area where the second multilayer film B6 is laminated. In FIG. 6A to 6C, the laminated sheet is formed by laminating the second multilayer film B6 on the most part of the region except for the region including peripheral portions of the sealant layer 30 and the first multilayer film layer A6. Both ends of one laminated sheet are stacked each other so as to be heat-sealed. According to the implementation illustrated in FIGS. 6A to 6C, the ratio of the area of the low air-permeability portion to the total internal area of the accommodating portion is 15%.

The second multilayer film B6 is provided on the outer surface's side of the outer bag for disposable body warmer packaging in FIGS. 6A to 6C. However, the first multilayer film A6 may be provided on the outer surface's side of the outer bag for disposable body warmer packaging in the same manner as the outer bag for disposable body warmer packaging of the fourth embodiment.

[Seventh Embodiment]

The seventh embodiment is a modified example of the sixth embodiment. The low air-permeability layer and the air-impermeable layer are provided on one sealant layer 30. The low air-permeability portion has the low air-permeability layer. The air-impermeable portion has the low air-permeability layer and the air-impermeable layer. Those that have been described above can be used without any limitation as the substrate, the low air-permeability layer and the air-impermeable layer, the sealant layer, and the like. In the seventh embodiment, two laminated sheets are stacked each other, and the peripheral portion thereof is four-side sealed. The portion where the low air-permeability layer and the air-impermeable layer are laminated constitutes the air-impermeable portion. The portion where the air-impermeable layer is not laminated constitutes the low air-permeability portion.

The features of the outer bag for disposable body warmer packaging according to the seventh embodiment will be described with reference to FIGS. 7A to 7C.

Figure 7A:
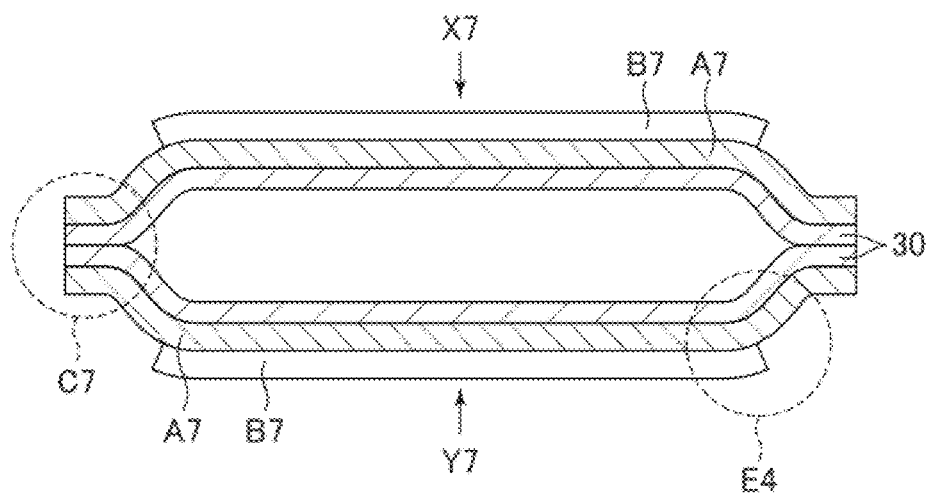
FIG. 7A is a cross-sectional view of an outer bag for disposable body warmer packaging in Embodiment 7 of the present invention.

FIG. 7A is a cross-sectional view. FIG. 7B(a) is a plan view where the outer bag is viewed in the direction of an arrow X7 in FIG. 7A. FIG. 7B(b) is a plan view where the outer bag is viewed in the direction of an arrow Y7 in FIG. 7A. FIG. 7C is a cross-sectional view illustrating a laminated state in the layered portion of a region including the neighborhood of the heat-sealed portion indicated by E4 in FIG. 7A.

In the seventh embodiment, two laminated sheets are formed by laminating the first multilayer film A7 on the sealant layer 30 over the entire area of the sealant layer 30 and laminating the second multilayer film B7 in a region at the central portion except for the peripheral portion of the first multilayer film A7. Two laminated sheets are stacked each other, and the peripheral portion thereof is four-side sealed. Thus, a bag can be formed, and the space in the bag becomes the accommodating portion of the disposable body warmer. The region adjacent to the heat-sealed portion does not include the second multilayer film B7. According to the implementation illustrated in FIGS. 7A to 7C, the two laminated sheets are stacked each other such that the sealant layer 30 is positioned on the inner surface's side of the outer bag and the second multilayer film B7 is positioned on the outer surface's side of the outer bag.

In FIG. 7A, the heat-sealed portion is indicated by C7.

Figure 7B:
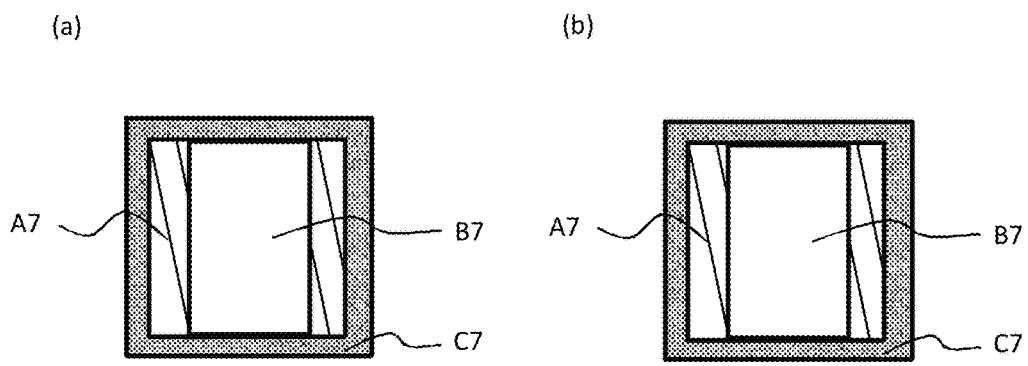
FIG. 7B is a plan view of the outer bag for disposable body warmer packaging in the Embodiment 7 of the present invention, where (a) is a plan view where the outer bag is viewed in the direction of an arrow X7 in FIG. 7A and (b) is a plan view where the outer bag is viewed in the direction of an arrow Y7 in FIG. 7A.
Figure 7C:
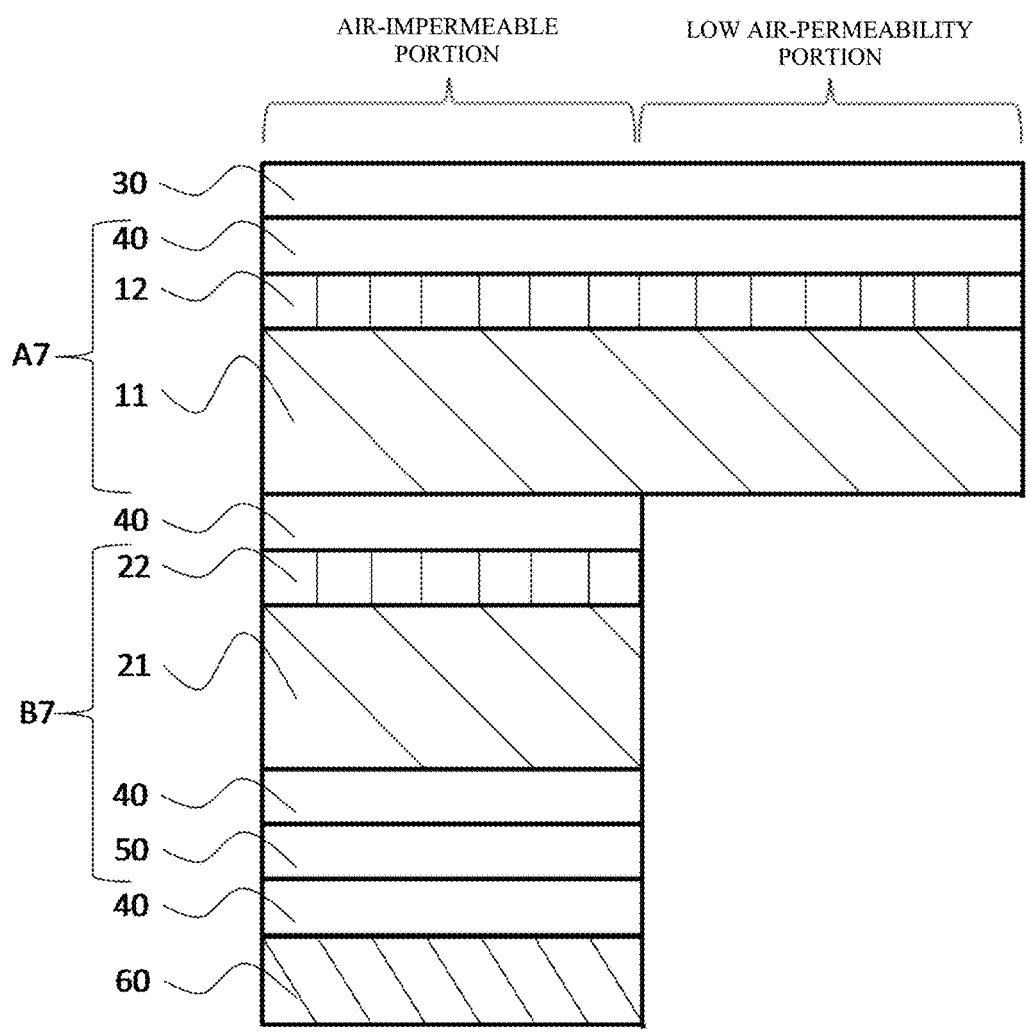
FIG. 7C is an explanatory view illustrating the layered structure of a cross section of a layered portion (E4 in FIG. 7A) of the outer bag for disposable body warmer packaging in the Embodiment 7 of the present invention.

As illustrated in FIG. 7C, the air-impermeable portion is constituted by laminating, when viewed from the outer surface's side of the outer bag, the additional resin layer 60, the adhesive layer 40, the printing ink layer 50, the adhesive layer 40, the second heat-resistant resin substrate 21, the vapor-deposited layer (air-impermeable layer) 22, the adhesive layer 40, the first heat-resistant resin substrate 11, the polyvinylidene chloride layer (low air-permeability layer) 12, the adhesive layer 40, and the sealant layer 30. In FIG. 7C, the low air-permeability portion adjacent to the heat-sealed portion of the laminated sheet is constituted by laminating, when viewed from the outer surface's side of the outer bag, the first heat-resistant resin substrate 11, the polyvinylidene chloride layer (low air-permeability layer) 12, the adhesive layer 40, and the sealant layer 30. The low air-permeability portion may be configured such that an adhesive layer 40, a printing ink layer 50, an adhesive layer 40, and an additional resin layer 60 are further laminated on the outer surface of the first heat-resistant resin substrate 11.

The area of the low air-permeability portion can be adjusted by changing the area where the second multilayer film B7 is laminated. In FIGS. 7A to 7C, the laminated sheet is formed by laminating the second multilayer film B7 on the most part of the region except for the region including the peripheral portions of the sealant layer 30 and the first multilayer film layer A7. Both ends of the two laminated sheets are stacked each other to be heat-sealed. In the neighborhood of the heat-sealed portion, the second multilayer film B7 is not laminated and the air-impermeable portion does not exist. According to the implementation illustrated in FIGS. 7A to 7C, the ratio of the area of the low air-permeability portion to the total internal area of the accommodating portion is 15%.

The second multilayer film B7 is provided on the outer surface's side of the outer bag for disposable body warmer packaging in FIGS. 7A to 7C. However, the first multilayer film A7 may be provided on the outer surface's side of the outer bag for disposable body warmer packaging in the same manner as in the outer bag for disposable body warmer packaging of the fourth embodiment.

The lamination conditions of the individual layers constituting the first multilayer film and the second multilayer film in the outer bag for disposable body warmer packaging of the present invention are not limited to those of the implementations described in the first embodiment to the seventh embodiment. For example, an implementation has been illustrated where the first heat-resistant resin substrate 11, the polyvinylidene chloride layer 12, and the sealant layer 30 are laminated in this order. But the lamination may be in the order of the polyvinylidene chloride layer 12, the first heat-resistant resin substrate 11, and the sealant layer 30.

The position of the sealant layer 30 in the outer bag for disposable body warmer packaging is not particularly limited, and it suffices that it is provided on the inner surface of the outer bag. But it may be provided on the outer surface of the outer bag. By providing the sealant layer 30 on the outer side of the polyvinylidene chloride layer 12, it is made possible to prevent the polyvinylidene chloride layer 12 from being damaged due to external contact and the gas barrier property from being impaired.

Also, the number and the shapes of low air-permeability portions and the air-impermeable portions in the outer bag for disposable body warmer packaging are not particularly limited, and may be selected from the group consisting of one or more circles, one or more quadrangles, one or more rectangles, one or more triangles, and combinations thereof.

The outer bag for disposable body warmer packaging of the present invention illustrated in FIGS. 1A to 7C includes a low air-permeability portion having an oxygen permeability of 1.5 to 20 cc/m$^2$·day·atm measured at 20° C. and 90% RH and having a water vapor permeability of 0.05 to 10 g/m$^2$·day measured at 40° C. and 90% RH; and an air-impermeable portion having an oxygen permeability of 1.3 cc/m$^2$·day·atm or lower measured at 20° C. and 90% RH and a water vapor permeability of 2.0 g/m$^2$·day or lower measured at 40° C. and 90% RH. Thereby, intrusion of oxygen into the inside of the outer bag from the outside of the outer bag is blocked to some extent, and permeation of hydrogen from the inside of the outer bag to the outside of the outer bag is allowed. By virtue of this, oxidation of metals such as the iron powders in the exothermic composition accommodated in the inner bag of the disposable body warmer is effectively prevented until it is used, and swelling of the outer bag due to hydrogen generated while it is stored is effectively prevented. Further, by including the low air-permeability portion and the air-impermeable portion, water vapor barrier property that inhibits permeation of water vapors is made higher. By virtue of this, intrusion of water into the inside of the outer bag from the outside of the outer bag can be prevented, also, the water contained as a constituent in the exothermic composition of the disposable body warmer and having the effect of promoting oxidation of metal such as iron powders, is prevented from being released as water vapor from the inside of the outer bag to the outside of the outer bag. In addition, it excels in the seal strength and impact resistance by virtue of the fact that it includes the low air-permeability portion and the air-impermeable portion. By virtue of this, it is made possible to prevent the outer bag from being opened or damaged even when it is exposed to a severe impact. Also, it excels in the weatherability by virtue of the fact that it includes the low air-permeability portion and the air-impermeable portion. As a result, change in the appearance such as change in the color is prevented even when the outer bag is exposed to ultraviolet rays such as sunlight.

Conventional publicly-known methods can be used as the method for manufacturing the multilayer film for the outer bag for disposable body warmer packaging and the outer bag for disposable body warmer packaging of the present invention.

For example, the first multilayer film A and the second multilayer film B can be produced by pressure bonding of the first heat-resistant resin substrate 11 having the polyvinylidene chloride layer 12 on its surface, the second heat-resistant resin substrate 21 having the vapor-deposited layer 22 on its surface, the adhesive layer 40, the printing ink layer 50, the additional resin layer 60, and the sealant layer 30, which are in a laminated state, by use of a roll or the like.

Next, the first multilayer film A and the second multilayer film B are stacked each other, the peripheral portion of the sealant layer 30 is heat-sealed, and thereby they are formed in the shape of a bag. Any mode usually used can be used as the mode of heat-sealing without any limitation, and, for example, any heat-sealing form such as lateral sealing, two-side sealing, three-side sealing, four-side sealing, envelope-seam sealing, butt-seam sealing (pillow sealing), pleat sealing, flat bottom sealing, square bottom sealing, and gusset sealing forms may be adopted. Any heat-sealing method usually used can be used as the heat-sealing method without any limitation, and for example, bar sealing, rotating roll sealing, belt sealing, impulse sealing, high-frequency sealing, and ultrasonic sealing may be adopted.

The width of the heat-sealed portion in the outer bag for disposable body warmer packaging of the present invention is preferably 1 to 30 mm, more preferably 3 to 20 mm, and most preferably 5 to 10 mm.

The outer bag for disposable body warmer packaging of the present invention has a width dimension of preferably 30 to 300 mm, more preferably 40 to 250 mm, and most preferably 50 to 200 mm; a length dimension of preferably 30 to 300 mm, more preferably 40 to 250 mm, and most preferably 50 to 200 mm; and a thickness of preferably 5 to 2000 μm, and more preferably 10 to 1500 μm.

The volume of the accommodating portion of the outer bag for disposable body warmer packaging of the present invention is preferably 1 to 5000 ml, more preferably 10 to 2000 ml, and most preferably 20 to 500 ml.

The disposable body warmer of the present invention is made by packaging airtightly an inner bag accommodating an exothermic composition, in the outer bag for disposable body warmer packaging.

The exothermic composition may be any exothermic composition usually used for the disposable body warmer and is not in particular limited. For example, an exothermic composition may be adopted which contains metal powder such as iron powder, a reaction aid such as sodium chloride, activated carbon, a water-retaining agent, water and the like. Specifically, for example, an exothermic composition can be formed from 100 parts by weight of metal powders, for example, iron powders such as reduced iron powders or cast iron powders, or aluminum powders, 3 to 10 parts by weight of a reaction aid such as sodium chloride, 20 to 40 parts by weight of activated carbon and a water-retaining agent, 30 to 90 parts by weight of water, and the like. Herein, for example, an alkali metal hydroxide and a weakly basic alkali metal salt such as sodium hydroxide, potassium hydroxide, sodium hydrogen carbonate and sodium tertiary phosphate can be added as a hydrogen generation inhibitor to the exothermic composition, and the amount thereof to be used can be a trace amount relative to the metal powders.

In addition, the inner bag accommodating the exothermic composition may be air-permeable to such an extent that a metal can generate heat in the presence of oxygen, and for example, a bag article where one surface is prepared by an air-permeable packaging material and the other surface is prepared by an air-impermeable packaging material, or a bag article where both surfaces are each prepared by an air-permeable packaging material can be used. As the air-permeable packaging material, for example, a woven fabric or a non-woven fabric, a porous sheet where a plastic film, sheet or the like is perforated, or a composite sheet thereof can be used. In addition, as the air-impermeable packaging material, films or sheets of, for example, a polyethylene-based resin, a polypropylene-based resin, an ethylene-propylene copolymer, an ethylene-vinyl acetate copolymer, an ionomer resin, an ethylene-ethyl acrylate copolymer, an ethylene-acrylic acid or methacrylic acid copolymer, a methylpentene polymer, a polybutene-based resin, a polyvinyl acetate-based resin, a poly(meth)acrylic-based resin, a polyacrylonitrile-based resin, a polystyrene-based resin, an acrylonitrile-styrene copolymer (AS-based resin), an acrylonitrile-butadiene-styrene copolymer (ABS-based resin), a polyester-based resin, a polyamide-based resin, a polycarbonate-based resin, a polyvinyl alcohol-based resin, a saponified product of an ethylene-vinyl acetate copolymer, a fluororesin, a diene-based resin, a polyacetal-based resin, a polyurethane-based resin, nitrocellulose, or other known resins can be used. Any commonly known method can be used as the method for producing the inner bag without any limitation, and for example, any of various heat-sealing methods described above with respect to production of the outer bag can be preferably used.

The inner bag in the disposable body warmer of the present invention has the width dimension of preferably 50 to 300 mm, more preferably 75 to 200 mm, and most preferably 100 to 170 mm, and the length dimension of preferably 50 to 300 mm, more preferably 75 to 200 mm, and most preferably 100 to 170 mm, and the thickness of preferably 5 to 2000 µm, and more preferably 10 to 1500 µm.

In the disposable body warmer of the present invention, the volume of the accommodating portion of the outer bag for disposable body warmer packaging per calorific value 1 kcal of the exothermic composition in the inner bag is preferably 0.03 to 150 ml, more preferably 0.3 to 80 ml, and most preferably 0.6 to 20 ml. In the disposable body warmer of the present invention, by defining the volume of the accommodating portion of the outer bag for disposable body warmer packaging per calorific value 1 kcal of the exothermic composition in the inner bag within the above-identified numerical ranges, it is made possible to achieve the effect that it is excellent in a gas barrier property that inhibits permeation of oxygen gas, water vapor and the like, which can allow swelling due to hydrogen gas generated during a storage period to be prevented.

EXAMPLES

The present invention will be described below further specifically with reference to examples and comparative examples.

Example 1

A laminated sheet which has the polyvinylidene chloride layer 12 laminated on the biaxially oriented polypropylene film 11 was prepared. The thickness of the biaxially oriented polypropylene film 11 is 30 µm and the thickness of the polyvinylidene chloride layer 12 is 1 µm. An ether-based adhesive was applied on the side of the polyvinylidene chloride layer 12 of the laminated sheet and was dried so as to form the adhesive layer 40. The straight-chain low density polyethylene film 30 (thickness of 30 µm) was placed on the laminated sheet via the adhesive layer 40 so as to be integrated therewith. Thereby, the laminated sheet which constitutes the low air-permeability portion (hereinafter referred to as "low air-permeability portion laminated sheet") was produced. The low air-permeability portion laminated sheet had the dimensions of a width of 120 mm and a length of 165 mm. The low air-permeability portion laminated sheet was obtained by laminating the first multilayer film A1 consisting of the adhesive layer 40/polyvinylidene chloride layer 12/biaxially oriented polypropylene film 11 when viewed from the lower layer's side of the low air-permeability portion laminated sheet, on the straight-chain low density polyethylene film 30.

In the meantime, the printing ink layer 50 was formed by printing a character, graphic, sign, pattern, and the like on one side of the biaxially oriented polypropylene film 60 (thickness of 20 µm) using gravure printing. Next, an ether-based adhesive was applied on the printing ink layer 50 and dried so as to form the adhesive layer 40. A laminated sheet having the aluminum vapor-deposited layer 22 laminated on the biaxially oriented polyethylene terephthalate film 21 (the thickness is 12 µm and the thickness of the vapor-deposited layer 22 is equal to or less than about 600 angstroms) was placed on and integrated with the adhesive layer 40 such that the adhesive layer 40 and the aluminum vapor-deposited layer 22 are brought into contact with each other. Further, the adhesive layer 40 was formed on the side opposite to the aluminum vapor-deposited layer 22 of the laminated sheet having the aluminum vapor-deposited layer 22 laminated on the biaxially oriented polyethylene terephthalate film 21. Then, the straight-chain low density polyethylene film 30 (thickness of 30 µm) was placed on the adhesive layer 40 and integrated therewith. The second multilayer film B1 consisting of the adhesive layer 40/biaxially oriented polyethylene terephthalate film 21/aluminum vapor-deposited layer 22/adhesive layer 40/printing ink layer 50 was positioned between the straight-chain low density polyethylene film 30 and the biaxially oriented polypropylene film 60. Thereby, a laminated sheet which constitutes an air-impermeable portion having the dimensions of a width of 120 mm and a length of 165 mm (hereinafter referred to as "air-impermeable portion laminated sheet") was produced.

In the same manner, sample laminated sheets were produced except that the thickness of the biaxially oriented polypropylene film 11 constituting the first multilayer film A1 was changed. Also, sample laminated sheets were produced using a biaxially oriented polyethylene terephthalate film 11 or a biaxially oriented polyamide film 11 in place of a biaxially oriented polypropylene film 11. Also, sample laminated sheets were produced except that the thickness of the biaxially oriented polyethylene terephthalate film 21 constituting the second multilayer film B1 was changed. A sample laminated sheet using a biaxially oriented polypropylene film 21 or a straight-chain low density polyethylene film 21 in place of a biaxially oriented polyethylene terephthalate film 21 was produced. A sample laminated sheet using an aluminum film in place of the laminated sheet having the aluminum vapor-deposited layer 22 laminated on the biaxially oriented polyethylene terephthalate film 21 was produced.

The oxygen permeability ($cc/(m^2 \cdot day \cdot atm)$) and the water vapor permeability were measured on the two types that have been obtained in this manner, i.e., the low air-permeability portion laminated sheet and the air-impermeable portion laminated sheet under the following conditions (1) and (2). The measurement results are shown in table 1.

(1) Measurement of Oxygen Permeability

The following measurement machine was used under the following measurement conditions to measure the oxygen permeability ($cc/(m^2 \cdot day \cdot atm)$) under the following temperature and humidity conditions.

Temperature: 20° C.; humidity: 90% RH

Measurement machine: OX-TRAN 2/20 manufactured by Mocon Inc.; measurement method: continuous measurement 20 times every 30 minutes (2) Measurement of Water Vapor Permeability The following measurement machine was used under the following measurement conditions to measure the water vapor permeability ($g/(m^2 \cdot day)$) under the following temperature and humidity conditions.

Temperature: 40° C.; humidity: 90% RH

Measurement machine: OX-TRAN 2/20 manufactured by Mocon Inc.; measurement method: continuous measurement 20 times every 30 minutes

[Table 1]

TABLE 1

| Film used | Resin component of substrate | Thickness of substrate (μm) | Oxygen permeability (cc/(m² · day · atm)) | Water vapor permeability (g/(m² · day)) |
|---|---|---|---|---|
| Low air-permeability portion | | | | |
| KOPP#30 | PP | 30 | 5.9 | 4.5 |
| KOPP#20 | PP | 20 | 5.9 | 4.6 |
| KOPP#40 | PP | 40 | 5.9 | 4.4 |
| KPET#12 | PET | 12 | 5.1 | 9.0 |
| KONY#15 | NY | 15 | 5.4 | 9.2 |
| Air-impermeable portion | | | | |
| VMPET#12 | PET | 12 | 0.9 | 0.7 |
| VMPET#9 | PET | 9 | 1.0 | 0.8 |
| VMPET#16 | PET | 16 | 0.8 | 0.6 |
| AL#7 | AL | 7 | 0.1 | 0.05 |

KOPP#30: a thickness of biaxially oriented polypropylene film 11 is 30 μm, a thickness of polyvinylidene chloride layer 12 is 1 μm
KOPP#20: a thickness of biaxially oriented polypropylene film 11 is 20 μm, a thickness of polyvinylidene chloride layer 12 is 1 μm
KOPP#40: a thickness of biaxially oriented polypropylene film 11 is 40 μm, a thickness of polyvinylidene chloride layer 12 is 1 μm
KPET#12: a thickness of biaxially oriented polyethylene terephthalate film 11 is 12 μm, a thickness of polyvinylidene chloride layer 12 is 1 μm
KONY#15: a thickness of biaxially oriented polyamide film 11 is 15 μm, a thickness of polyvinylidene chloride layer 12 is 1 μm
VMPET#12: a thickness of biaxially oriented polyethylene terephthalate film 21 is 12 μm, a thickness of vapor-deposited layer 22 is about 600 angstroms or less
VMPET#9: a thickness of biaxially oriented polyethylene terephthalate film 21 is 9 μm, a thickness of vapor-deposited layer 22 is about 600 angstroms or less
VMPET#16: a thickness of biaxially oriented polyethylene terephthalate film 21 is 16 μm, a thickness of vapor-deposited layer 22 is about 600 angstroms or less
AL#7: a thickness of aluminum film is 7 μm Example 2

The following (3) Evaluation of appearance after acceleration test and (4) Evaluation of exothermic performance (duration) after acceleration test were conducted on the laminated sheet of the sample produced in the Example 1. The evaluation results are shown in Table 4.

(3) Evaluation of Appearance after Acceleration Test

The laminated sheet of the sample produced in the Example 1 was positioned as illustrated in the Embodiment 1 (FIGS. 1A to 1C). The low air-permeability portion laminated sheet and the air-impermeable portion laminated sheet were stacked such that the ratios of the areas of the low air-permeability portion and the air-impermeable portion to the total internal area of the accommodating portion of the outer bag for disposable body warmer packaging each become 50%. Then, its peripheral portion was three-side heat-sealed to form a heat-sealed portion. Thereby, a three-sides heat-sealed outer bag for disposable body warmer packaging was produced. The three-sides heat-sealed outer bag had the dimensions of: a width of 120 mm; a length of 165 mm; and a thickness of 130 μm, and had an opening at an upper portion thereof.

An exothermic composition including 22 g of iron powder, 6 g of activated carbon, 6 g of a water-retaining agent, and 10 g of water was prepared. The exothermic composition was then charged and packaged in an inner bag to produce a stick type disposable body warmer. The inner bag comprised an air-permeable porous sheet made of a polyethylene film and an air-impermeable sheet made of a polyethylene film adhered to each other. The stick type disposable body warmer included an individual package and had the dimensions of: a width of 95 mm; a length of 130 mm; and a thickness of 5 mm.

Next, the disposable body warmer including an individual package, produced as described above, was charged through the opening portion of the outer bag for disposable body warmer packaging produced as described above. Thereafter the opening portion was heat-sealed to form an upper sealed portion. Thereby, a disposable body warmer product having the size of a width of 120 mm; a length of 165 mm; and a thickness of 5.2 mm was produced. The disposable body warmer obtained in this manner showed that the volume of the accommodating portion of the outer bag for disposable body warmer packaging per 1 kcal of calorific value of the exothermic composition within the inner bag was 2.62 ml.

Five of the disposable body warmer products thus obtained were placed on a stage. The height (mm) of the five disposable body warmer products stacked (hereinafter, referred to as "height H1 (mm)") was measured. Next, the five disposable body warmer products stacked were stored at a temperature of 50° C. for three months. The height (mm) of the five disposable body warmer products stacked was measured every week for a period of three months. The height after a lapse of three months was defined as "height H2 (mm)." If any outer bag of the disposable body warmer products was swollen and broken during the storage period, the maximum height before such breakage was defined as the "height H2 (mm)." The value "H2−H1 (mm)" was then calculated, and rated as the appearance after an acceleration test, according to the following criteria of Table 2.

[Table 2]

TABLE 2

| | |
|---|---|
| −3 < H2 − H1 (mm) < 3: | No change |
| −5 < H2 − H1 (mm) ≤ −3: | Slightly depressurizing tendency |
| H2 − H1 (mm) ≤ −5: | Depressurizing tendency |
| 3 ≤ H2 − H1 (mm) < 5: | Slightly swelling tendency |
| 5 ≤ H2 − H1 (mm): | Swelling tendency |

(4) Evaluation of Exothermic Performance (Duration) after Acceleration Test

A disposable body warmer product was produced in the same manner as in "(3) Evaluation of appearance after acceleration test" above.

The outer bags for disposable body warmer of ten of the disposable body warmer products thus obtained were opened to take out respective disposable body warmers. The exothermic performance of each of the disposable body warmers was tested based on JIS S4100. The duration average was defined as the "exothermic performance (duration)·initial" (hereinafter, referred to as "duration T1").

On the other hand, the ten disposable body warmer products obtained above were stored at a temperature of 50° C. for three months. Thereafter, respective outer bags for disposable body warmer were opened to take out respective disposable body warmers. The exothermic performance of each of the disposable body warmers was tested based on JIS S4100. The duration average was defined as "exothermic performance (duration)·after acceleration test" (hereinafter, referred to as "duration T2").

The value of T2/T1×100(%) was then calculated, and rated as the exothermic performance (duration) after an acceleration test, according to the following criteria of Table 3.

[Table 3]

TABLE 3

| | |
|---|---|
| 95 < T2/T1 × 100(%) ≤ 100: | ⊚ (Excellent) |
| 90 < T2/T1 × 100(%) ≤ 95: | ○ (Favorable) |
| 80 < T2/T1 × 100(%) ≤ 90: | Δ (Usable) |
| T2/T1 × 100(%) ≤ 80: | X (Not suitable as product) |

The heat-sealed portion was broken due to swelling, and heat generation was terminated before product opening:

- (Not suitable as product)

[Table 4]

TABLE 4

| No. | Film included in low air-permeability portion | Film included in air-impermeable portion | H2 − H1 (mm) | Evaluation of appearance | Exothermic performance (duration) |
|---|---|---|---|---|---|
| 1 | KOPP#30 | VMPET#12 | 0 | No change | ⊚ |
| 2 | KOPP#20 | VMPET#12 | 0 | No change | ⊚ |
| 3 | KOPP#40 | VMPET#12 | 0 | No change | ⊚ |
| 4 | KOPP#30 | VMPET#9 | −1 | No change | ⊚ |
| 5 | KOPP#30 | VMPET#16 | 1 | No change | ⊚ |
| 6 | KPET#12 | VMPET#12 | −2 | No change | ○ |
| 7 | KONY#15 | VMPET#12 | −2 | No change | ○ |

*The ratios of the areas of the low air-permeability portion and the air-impermeable portion to the total internal area of the accommodating portion are 50%, respectively.

Example 3

In the same manner as in the Example 1, low air-permeability portion laminated sheet was produced. The low air-permeability portion laminated sheet was obtained by laminating the first multilayer film A1 composed of the adhesive layer 40/polyvinylidene chloride layer 12/biaxially oriented polypropylene film 11 when viewed from the lower layer's side of the low air-permeability portion laminated sheet on the straight-chain low density polyethylene film 30. The low air-permeability portion laminated sheet had the dimensions of: a width of 120 mm and a length of 165 mm.

Meanwhile, in the same manner as in the Example 1, a low air-permeability portion laminated sheet and an air-impermeable portion laminated sheet were produced. The low air-permeability portion laminated sheet had the dimensions and was obtained by laminating the first multilayer film A1 composed of the adhesive layer 40/polyvinylidene chloride layer 12/biaxially oriented polypropylene film 11 on a straight-chain low density polyethylene film 30. In the air-impermeable portion laminated sheet, the second multilayer film B1 composed of the adhesive layer 40/biaxially oriented polyethylene terephthalate film 21/aluminum vapor-deposited layer 22/adhesive layer 40/printing ink layer 50 is positioned between the straight-chain low density polyethylene film 30 and the biaxially oriented polypropylene film 60. The straight-chain low density polyethylene films 30 which were the sealant layers of these laminated sheets were stacked each other within the range of 5 mm from the end of one side thereof. Then, the end of the one side is heat-sealed, and thus a laminated sheet was produced such that the dimensions are given as a width of 120 mm and a length of 165 mm. In the laminated sheet, the ratio of the low air-permeability portion laminated sheet to the total internal surface area was defined as 50% and the ratio of the air-impermeable portion laminated sheet to the total internal surface area was defined as 50%.

Two of the laminated sheets thus obtained were positioned as illustrated in the Embodiment 2 (FIGS. 2A to 2C). The low air-permeability portion laminated sheet and the air-impermeable portion laminated sheet were placed on each other such that the ratio of the area of the low air-permeability portion to the total internal area of the accommodating portion of the outer bag for disposable body warmer packaging becomes 75% and the ratio of the area of the air-impermeable portion to the total internal area of the accommodating portion becomes 25%. Then, the peripheral portion thereof was three-sides heat-sealed so as to form a heat-sealed portion. Thereby, an outer bag for disposable body warmer packaging of a three-sides sealed type having the dimensions of a width of 120 mm, a length of 165 mm, and a thickness of 130 μm and having an opening at an upper portion thereof was produced.

A disposable body warmer product was produced in the same manner as in the Example 2 using the outer bag for disposable body warmer packaging thus obtained.

In the same manner, the body warmer products were produced except that the ratios of the areas of the low air-permeability portion and the air-impermeable portion to the total internal area of the accommodating portion of the outer bag for disposable body warmer packaging are changed as shown in Table 5.

(3) Evaluation of appearance after acceleration test and (4) Evaluation of exothermic performance (duration) after acceleration test were conducted on the disposable body warmer product thus obtained in the same manner as in the Example 2. The evaluation results are shown in Nos. 8 to 11 of Table 5.

Example 4

In the same manner as in the Example 1, a low air-permeability portion laminated sheet was produced. The low air-permeability portion laminated sheet was obtained by laminating the first multilayer film A1 composed of adhesive layer 40/polyvinylidene chloride layer 12/biaxially oriented polypropylene film 11 when viewed from the lower layer's side of the low air-permeability portion laminated sheet, on the straight-chain low density polyethylene film 30. The low air-permeability portion laminated sheet had the dimensions of a width of 120 mm and a length of 165 mm.

Meanwhile, in the same manner as in the Example 1, an aluminum vapor-deposited air-impermeable portion laminated sheet and an aluminum film air-impermeable portion laminated sheet were produced. In the aluminum vapor-deposited air-impermeable portion laminated sheet, the second multilayer film B1 composed of the adhesive layer 40/biaxially oriented polyethylene terephthalate film 21/aluminum vapor-deposited layer 22/adhesive layer 40/printing ink layer 50 was positioned between the straight-chain low density polyethylene film 30 and the biaxially oriented polypropylene film 60. In the aluminum film air-impermeable portion laminated sheet, the second multilayer film B1' composed of the adhesive layer 40/aluminum film/adhesive layer 40/printing ink layer 50 is positioned between the straight-chain low density polyethylene film 30 and the biaxially oriented polypropylene film 60. The straight-chain low density polyethylene films 30 which are the sealant layers of the aluminum vapor-deposited air-impermeable portion laminated sheet and the aluminum film air-impermeable portion laminated sheet are stacked each other within the range of 5 mm from the end of one side thereof. The end of the one side thereof is then heat-sealed, and thus an air-impermeable portion laminated sheet was produced such that the dimensions are given as a width of 120 mm and a length of 165 mm. In the air-impermeable portion laminated sheet, the ratio of the aluminum vapor-deposited air-impermeable portion laminated sheet to the entire surface area is defined as 50% and the ratio of the aluminum film air-impermeable portion laminated sheet to the entire surface area is defined as 50%.

Also, the low air-permeability portion laminated sheet, the aluminum vapor-deposited air-impermeable portion laminated sheet, and the aluminum film air-impermeable portion laminated sheet were positioned as illustrated in the modified example of the embodiment 2 (FIG. 2D). They were stacked each other such that the ratios of the areas of the low air-permeability portion laminated sheet, the aluminum vapor-deposited air-impermeable portion laminated sheet, and the aluminum film air-impermeable portion laminated sheet to the total internal surface of the accommodating portion of the outer bag for disposable body warmer packaging become 50%, 25%, and 25% respectively so as to be heat-sealed. Then, the peripheral portion thereto was three-sides heat-sealed so as to form a heat-sealed portion. Thereby, a three-sides heat-sealed outer bag for disposable body warmer packaging having the dimensions of: a width of 120 mm; a length of 165 mm; and a thickness of 130 μm and having an opening at an upper portion thereof was produced.

A disposable body warmer product was produced in the same manner as in the Example 2 using the outer bag for disposable body warmer packaging thus obtained. (3) Evaluation of appearance after acceleration test and (4) Evaluation of exothermic performance (duration) after acceleration test were conducted on the disposable body warmer product. The evaluation results are shown in No. 12 of Table 5.

[Table 5]

TABLE 5

| No. | Ratio of area of low air-permeability portion (%) | Ratio of area of air-impermeable portion (%) | H2 − H1 (mm) | Evaluation of appearance | Exothermic performance (duration) |
|---|---|---|---|---|---|
| 8 | 75*1 | 25*2 | −2 | No change | ○ |
| 9 | 25*1 | 75*2 | 2 | No change | ◎ |
| 10 | 20*1 | 80*2 | 3 | No change | ◎ |
| 11 | 15*1 | 85*2 | 4 | Slightly swelling tendency | ◎ |
| 12 | 50*1 | 25/25*3 | 0 | No change | ◎ |

*1Film included in the low air-permeability portion: KOPP#30
*2Film included in the air-impermeable portion: VMPET#12
*3Film included in the air-impermeable portion: VMPET#12 50% and AL#7 50%

Comparative Example 1

A printing ink layer and an adhesive layer were formed in the same manner as in the Example 1 on one side of the biaxially oriented polypropylene film (thickness of 20 μm) in the same manner as in the Example 1 except that the polyvinylidene chloride layer and the vapor-deposited layer are not included. A straight-chain low density polyethylene film (having a thickness of 30 μm) is placed on this adhesive layer to be laminated on and integrated with it. Thereby, a laminated sheet which is high air-permeability portion (hereinafter referred to as "high air-permeability portion laminated sheet") was produced such that its dimensions are given as a width of 120 mm and a length of 165 mm. The high air-permeability portion laminated sheet was made of a straight-chain low density polyethylene film/adhesive layer/printing ink layer/biaxially oriented polypropylene film when viewed from the lower surface's side of the laminated sheet.

The oxygen permeability (cc/(m²·day·atm)) and the water vapor permeability were measured on the high air-permeability portion laminated sheet thus obtained under conditions (1) and (2) in the same manner as in the Example 1. The measurement results are shown in Table 6.

Also, two of the high air-permeability portion laminated sheets thus obtained were stacked each other in the same manner as in the Example 2. Thus, a three-sides heat-sealed type of the outer bag for disposable body warmer packaging having an opening at an upper portion thereof was produced.

Comparative Example 2

The high air-permeability portion laminated sheet produced in the Comparative Example 1 and the air-impermeable portion laminated sheet produced in the Example 1 were stacked each other in the same manner as in the Example 3, such that the ratio of the area of the high air-permeability portion to the total internal surface of the accommodating portion of the outer bag for disposable body warmer packaging becomes 10%, and the ratio of the area of the air-impermeable portion to the total internal surface of the accommodating portion becomes 90%. Thus, a three-sides heat-sealed type of the outer bag for disposable body warmer packaging having an opening at an upper portion thereof was produced. The air-impermeable portion laminated sheet included a laminated sheet having the aluminum vapor-deposited layer 22 laminated on the biaxially oriented polyethylene terephthalate film 21.

Comparative Examples 3 to 5

The outer bags for disposable body warmer packaging having low air-permeability portion 100% or air-impermeable portion 100% were produced using only one type of the laminated sheet of the sample produced in the Example 1 in the same manner as in the Example 2.

In addition, (3) Evaluation of appearance after acceleration test and (4) Evaluation of exothermic performance (duration) after acceleration test were conducted on the outer bags for disposable body warmer packaging of the Comparative Examples 1 to 5 in the same manner as in the Example 2. The evaluation results are shown in Table 6.

each heat-sealed portion to be broken. Each body warmer was brought into contact with outside air to terminate heat generation before each product was opened.

Also, the exothermic composition was charged and packaged in an inner bag to produce a non-stick type disposable body warmer including an individual package. The inner bag comprises an air-permeable perforated sheet made of a polyethylene film and an air-impermeable sheet made of a polyethylene film adhered to each other. The disposable body warmer was tested in the same manner as in the Examples Nos. 1 to 12. The favorable results were similarly obtained as in the Examples Nos. 1 to 12.

TABLE 6

| Comparative example | Film used | Oxygen permeability (cc/($m^2$·day·atm)) | Water vapor permeability (g/($m^2$·day)) | Area ratio (%) | H2-H1 (mm) | Evaluation of appearance | Exothermic performance (duration) |
|---|---|---|---|---|---|---|---|
| 1 | OPP#20 | 1000 | 8.0 | 100% | −10 | Depressurizing tendency | x |
| 2 | OPP#20 | 1000 | 8.0 | 10% | −9 | Depressurizing tendency | x |
|   | VMPET#12 | 0.9 | 0.7 | 90% |   |   |   |
| 3 | KOPP#20 | 5.9 | 4.5 | 100% | −8 | Depressurizing tendency | x |
| 4 | VMPET#12 | 0.9 | 0.7 | 100% | 13 | Swelling tendency | — |
| 5 | AL#7 | 0.1 | 0.05 | 100% | 15 | Swelling tendency | — |

When the rating of the appearance in the above Tables 4 to 6 is "No change," "Slightly depressurizing tendency," or "Slightly swelling tendency," a disposable body warmer product is not changed in appearance even after storage for a long period and thus can be sold into a market as a product. On the other hand, when the rating of the appearance in Tables 4 to 6 is "Depressurizing tendency" or "Swelling tendency," a disposable body warmer product is not preferable because of being changed in appearance after storage for a long period.

As will be appreciated from the results in the above Tables 4 to 6, in Examples 1 to 10 and 12, no change in appearance of a package product was observed before and after an acceleration test and no degradation in exothermic function as a product was caused even after storage for a long period. In addition, in Examples 1 to 12, the outer bag for disposable body warmer packaging was low in water vapor permeability, allowing water vapor to not easily penetrate. Thereby, moisture did not easily penetrate from the exterior into the interior of the outer bag, and moisture included as a component of the disposable body warmer did not easily escape to the outside. Therefore, they served sufficiently as a disposable body warmer even after storage for a long period.

On the other hand, in Comparative Examples 1 to 5, any change in appearance of a package product was observed before and after an acceleration test and each disposable body warmer product was not preferable in terms of appearance after storage for a long period. In addition, in Comparative Examples 1 to 3, each outer bag was slightly high in water vapor permeability and causing water vapor to easily penetrate. Thereby, moisture did not easily penetrate from the exterior into the interior of the outer bag, and moisture included as an exothermic composition component of each disposable body warmer did not easily escape to the outside. Therefore, they did not sufficiently generate heat as a disposable body warmer after storage for a long period. Furthermore, in Comparative Examples 4 and 5, swelling tendency was remarkably observed. Such swelling caused

REFERENCE SIGNS LIST

A1 to A7 multilayer film for outer bag for disposable body warmer packaging
11 heat-resistant resin substrate
12 polyvinylidene chloride layer
B1 to B7 multilayer film for outer bag for disposable body warmer packaging
21 heat-resistant resin substrate
22 vapor-deposited layer
30 sealant layer
40 adhesive layer
50 printing ink layer
60 additional resin layer

The invention claimed is:

1. An outer bag for disposable body warmer packaging having an accommodating potion accommodating a disposable body warmer accommodated in an air-permeable inner bag, the outer bag comprising:
   a low air-permeability portion having an oxygen permeability of 1.5 to 20 cc/$m^2$·day·atm measured at 20° C. and 90% RH and a water vapor permeability of 0.05 to 10 g/$m^2$·day measured at 40° C. and 90% RH; and an air-impermeable portion having an oxygen permeability of 1.3 cc/$m^2$·day·atm or lower measured at 20° C. and 90% RH and a water vapor permeability of 2.0 g/$m^2$·day or lower measured at 40° C. and 90% RH, and wherein a ratio of an area of the low air-permeability portion to a total internal area of the accommodating portion is 15 to 75%.

2. The outer bag for disposable body warmer packaging according to claim 1, wherein a ratio of area of the low air-permeability portion to a total internal area of the accommodating portion is 50%.

3. The outer bag for disposable body warmer packaging according to claim 1, wherein the outer bag for disposable body warmer packaging has at least one heat-sealed portion formed by heat-sealing one or more laminated sheets, and the low air-permeability portion is provided in at least a part of a region adjacent to the heat-sealed portion.

4. A disposable body warmer packaged by the outer bag according to claim 1.

5. The outer bag for disposable body warmer packaging according to claim 1, wherein the low air-permeability portion has a first substrate and a low air-permeability layer laminated on the first substrate, and the air-impermeable portion has a second substrate and an air-impermeable layer laminated on the second substrate, and the first substrate and the second substrate are heat-sealed.

6. The outer bag for disposable body warmer packaging according to claim 5, wherein the low air-permeability layer comprises a homopolymer or copolymer of vinylidene chloride, and the air-impermeable layer contains a metal or metal oxide.

7. The outer bag for disposable body warmer packaging according to claim 1, wherein a low air-permeability layer and an air-impermeable layer are provided on one sealant layer, and the low air-permeability portion has the low air-permeability layer, and the air-impermeable portion has the air-impermeable layer.

8. The outer bag for disposable body warmer packaging according to claim 7, wherein the low air-permeability layer comprises a homopolymer or copolymer of vinylidene chloride, and the air-impermeable layer contains a metal or metal oxide.

9. The outer bag for disposable body warmer packaging according to claim 1, wherein a low air-permeability layer and an air-impermeable layer are provided on one sealant layer, and the low air-permeability portion has the low air-permeability layer, and the air-impermeable portion has the low air-permeability layer and the air-impermeable layer.

10. The outer bag for disposable body warmer packaging according to claim 9, wherein the low air-permeability layer comprises a homopolymer or copolymer of vinylidene chloride, and the air-impermeable layer contains a metal or metal oxide.

* * * * *